(12) United States Patent
Abuhamad

(10) Patent No.: US 8,083,678 B2
(45) Date of Patent: Dec. 27, 2011

(54) SYSTEM, METHOD AND MEDIUM FOR ACQUIRING AND GENERATING STANDARDIZED OPERATOR INDEPENDENT ULTRASOUND IMAGES OF FETAL, NEONATAL AND ADULT ORGANS

(75) Inventor: Alfred Z. Abuhamad, Virginia Beach, VA (US)

(73) Assignee: Eastern Virginia Medical School, Norfolk, VA (US)

( * ) Notice: Subject to any disclaimer, the term of this patent is extended or adjusted under 35 U.S.C. 154(b) by 1161 days.

(21) Appl. No.: 11/089,040

(22) Filed: Mar. 25, 2005

(65) Prior Publication Data

US 2005/0251036 A1 Nov. 10, 2005

Related U.S. Application Data

(63) Continuation-in-part of application No. 10/823,793, filed on Apr. 14, 2004.

(60) Provisional application No. 60/463,045, filed on Apr. 16, 2003.

(51) Int. Cl.
*A61B 8/00* (2006.01)

(52) U.S. Cl. .................. 600/443; 600/437

(58) Field of Classification Search .......... 600/437, 600/441, 443, 445, 447, 461; 128/916, 922; 345/427

See application file for complete search history.

(56) References Cited

U.S. PATENT DOCUMENTS

| | | | | |
|---|---|---|---|---|
| 5,159,931 A * | 11/1992 | Pini | | 600/443 |
| 5,538,003 A * | 7/1996 | Gadonniex et al. | | 600/445 |
| 5,605,155 A | 2/1997 | Chalana et al. | | |
| 5,787,889 A * | 8/1998 | Edwards et al. | | 600/443 |
| 5,872,571 A * | 2/1999 | Arling | | 345/427 |
| 5,957,844 A * | 9/1999 | Dekel et al. | | 600/439 |
| 5,964,707 A * | 10/1999 | Fenster et al. | | 600/443 |
| 6,102,866 A * | 8/2000 | Nields et al. | | 600/461 |
| 6,174,285 B1 * | 1/2001 | Clark | | 600/443 |
| 6,290,648 B1 * | 9/2001 | Kamiyama | | 600/443 |
| 6,306,089 B1 * | 10/2001 | Coleman et al. | | 600/437 |
| 6,375,616 B1 * | 4/2002 | Soferman et al. | | 600/443 |
| 6,443,896 B1 * | 9/2002 | Detmer | | 600/445 |
| 6,470,092 B1 | 10/2002 | Li et al. | | |
| 6,544,178 B1 * | 4/2003 | Grenon et al. | | 600/443 |
| 6,683,973 B2 | 1/2004 | Li et al. | | |

(Continued)

FOREIGN PATENT DOCUMENTS

JP 11299782 A 11/1999

(Continued)

OTHER PUBLICATIONS

Nelson et al., "Fetal Heart Assessment Using Three-Dimensional Ultrasound," In Merz ed. 3D Ultrasound in Obstetrics and Gynecology, Lippincott Williams and Wilkins, 1998.*

(Continued)

*Primary Examiner* — Long V. Le
*Assistant Examiner* — Angela M Hoffa
(74) *Attorney, Agent, or Firm* — Dean D. Small; The Small Patent Law Group

(57) ABSTRACT

A system, method and medium for standardizing a manner of acquisition and display of ultrasound images. In one embodiment of the invention, a volumetric image of an organ is acquired in a standardized manner. Relationships such as formulas are utilized to automatically generate anatomical planes of interest within the volume that can be displayed independent of the user.

14 Claims, 39 Drawing Sheets

U.S. PATENT DOCUMENTS

| | | | |
|---|---|---|---|
| 6,709,394 B2 * | 3/2004 | Frisa et al. | 600/445 |
| 7,024,024 B1 * | 4/2006 | Aiazian | 382/128 |
| 2002/0133075 A1 * | 9/2002 | Abdelhak | 600/443 |
| 2003/0055308 A1 | 3/2003 | Friemel et al. | |
| 2005/0004465 A1 * | 1/2005 | Abuhamad | 600/443 |
| 2005/0101864 A1 * | 5/2005 | Zheng et al. | 600/443 |

FOREIGN PATENT DOCUMENTS

| | | |
|---|---|---|
| JP | 2003-325513 A | 11/2003 |
| JP | 2004-517660 T | 6/2004 |
| WO | WO 98/47428 | 10/1998 |
| WO | WO 00/58754 | 10/2000 |
| WO | WO 02/43562 A2 | 6/2002 |

OTHER PUBLICATIONS

Supplementary European Search Report dated Mar. 9, 2010, Application No. 06748703.3-2319 / 1861016, Patent No. PCT/US2006/010990, (9) pages.

Goncalves, et al., Four-Dimensional Ultrasonography of the Fetal Heart With Spatiotemporal Image Correlation, American Journal of Obstetrics & Gynecology, vol. 189, No. 6, (12) pages.

Eberhard Merz, Three-Dimensional Transvaginal Ultrasound in Gynecological Diagnosis, Ultrasound Obstet Gynecol 1999:14, 81-86.

Sohaey, R. and Zweibel, WJ, The Fetal Heart: A Practical Sonographic Approach, Semin Ultrasound CT MR, Feb. 1996; 17(1): 15-33.

Supplementary European Search Report under Article 153(7) for Application No. EP 04 75 9845.3-1265 / 1620014, PCT/US2004/011397, dated May 19, 2009, (5) pages.

Abuhamad, Alfred Z. et al. 2004. "The Accreditation of Ultrasound Practices: Impact on Compliance with Minimum Performance Guidelines." *Journal of Ultrasound Medicine.* 23; 1023-1029.

Rotten, D. et al. 2004. "Two- and Three-Dimensional Sonographic Assessment of the Fetal Face. 1. A Systematic Analysis of the Normal Face." *Ultrasound Obstet. Gynecol.* 23; 224-231.

Klein, S.K. et al. 1999. "Efficacy of Routine Fetal Ultrasound Screening of Congenital Heart Disease in Isere Country, France." *Prenatal Diagnosis.* 19; 318-322.

Stoll, C. et al. 1998. "Evaluation of Prenatal Diagnosis of Congenital Heart Disease." *Prenatal Diagnosis.* 18; 801-807.

Todros, Tullia et al. 1997. "Accuracy of Routine Ultrasonography in Screening Heart Disease Prenatally." *Prenatal Diagnosis.* 17; 10; 901-906.

Buskens, E. 1996. "Efficacy of Routine Fetal Ultrasound Screening for Congenital Heart Disease in Normal Pregnancy." *Circulation.* 94; 67-72.

Ewigman, Bernard G. et al. 1993. "Effect of Prenatal Ultrasound Screening on Perinatal Outcome." *The New England Journal of Medicine.* vol. 329; 821-827.

Japanese Language document: The Japan Society of Ultrasonics in Medicine, ed., Ultrasound Diagnosis, vol. 1, Igaku-Shoin Ltd., May 1, 1998, pp. 628-631, pp. 658-660, pp. 664-665.

* cited by examiner

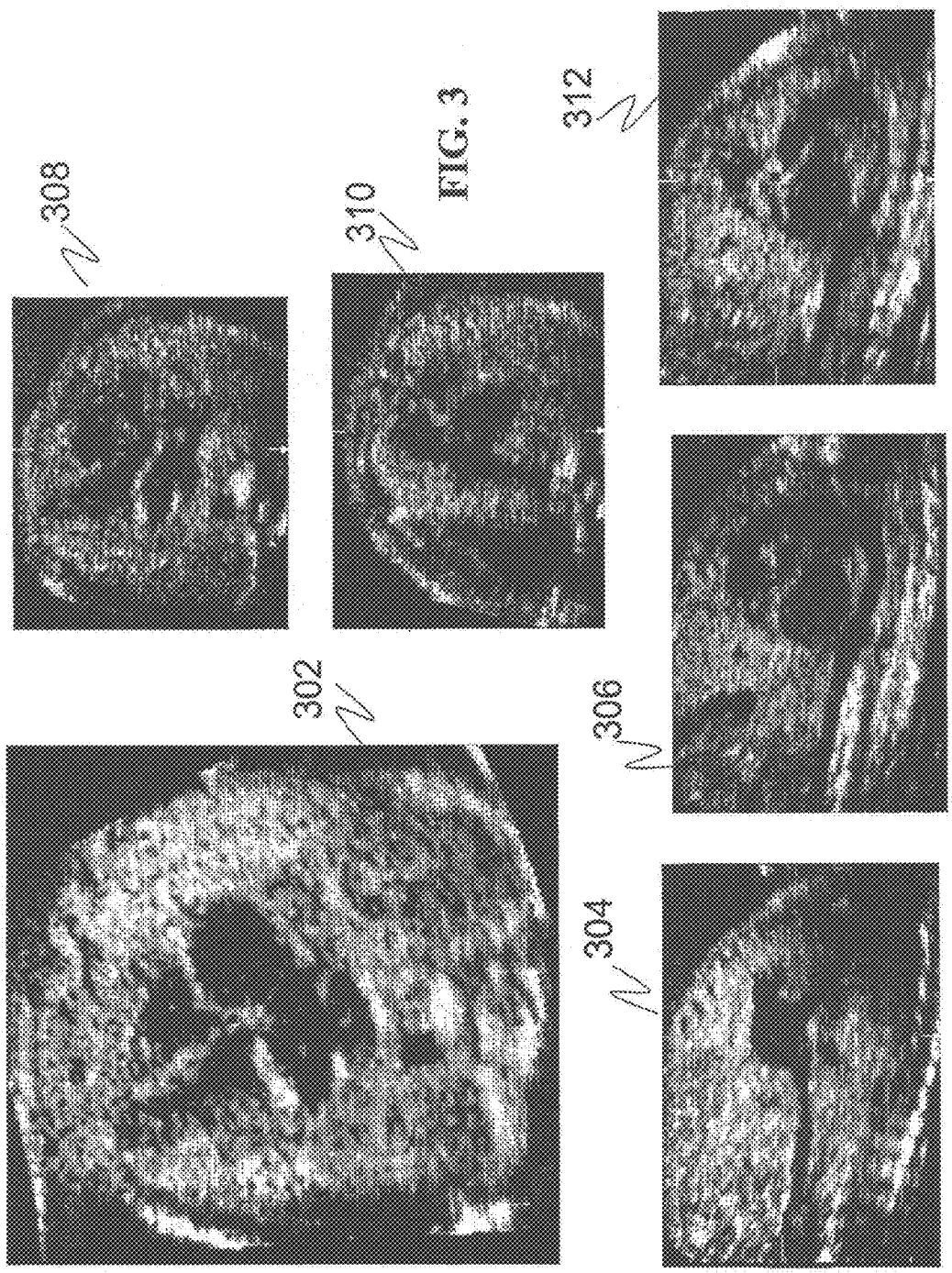

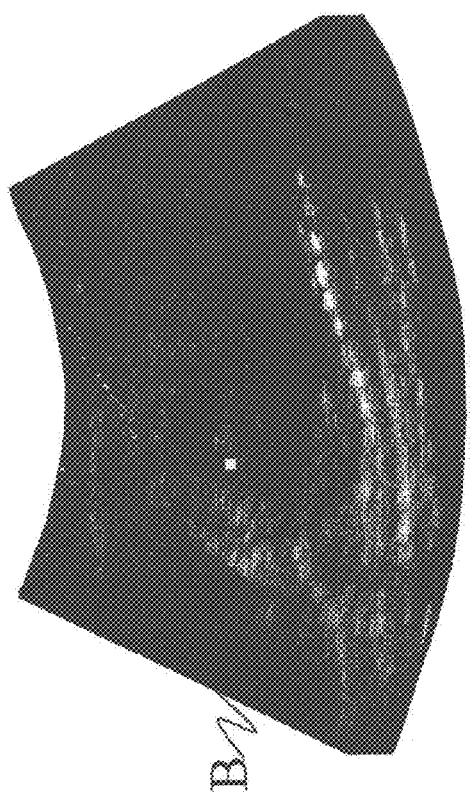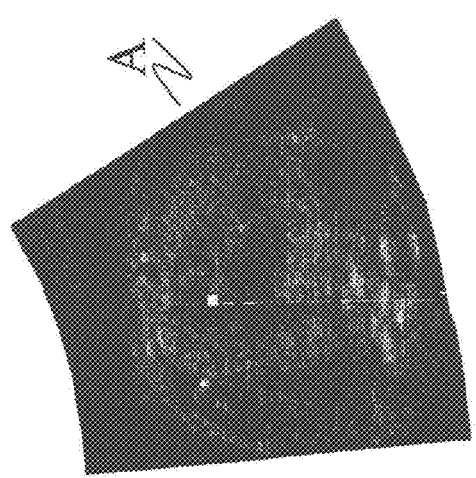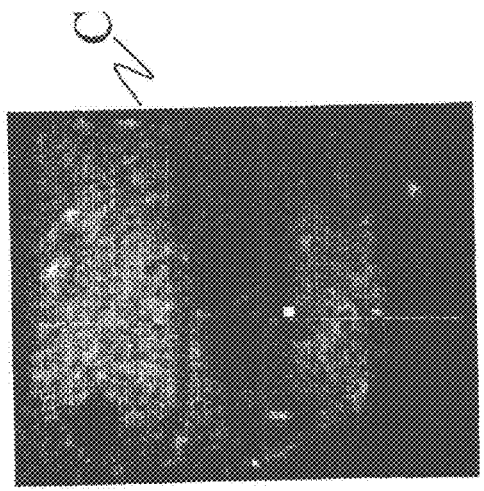
FIG. 5

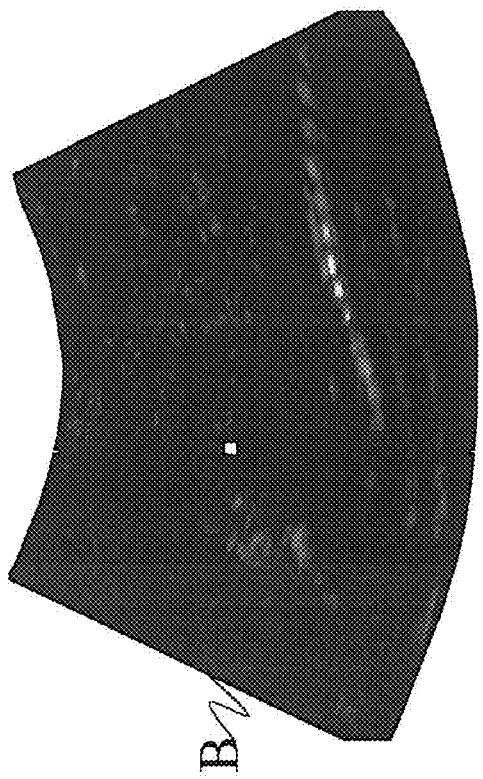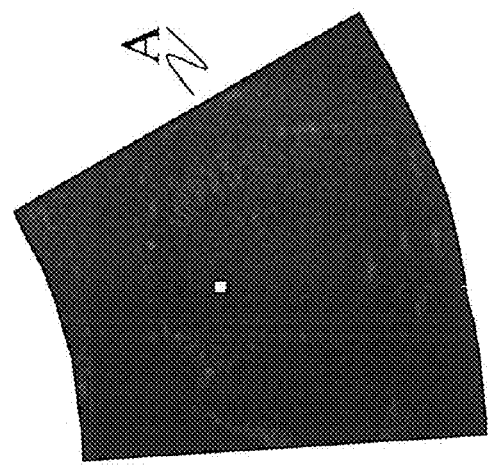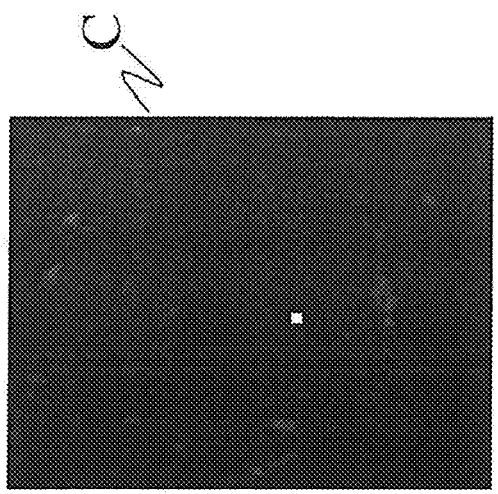
FIG. 6

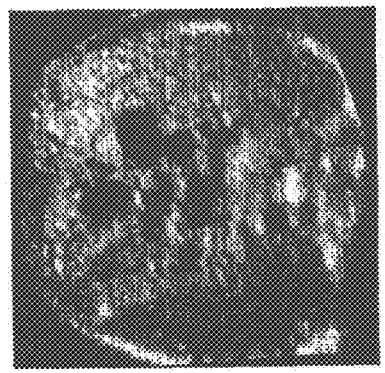
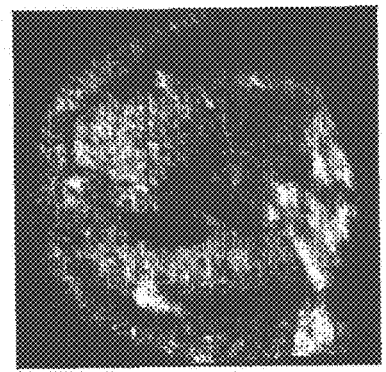
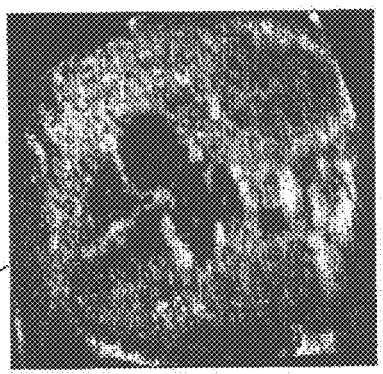
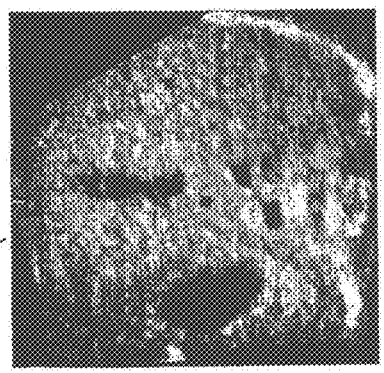
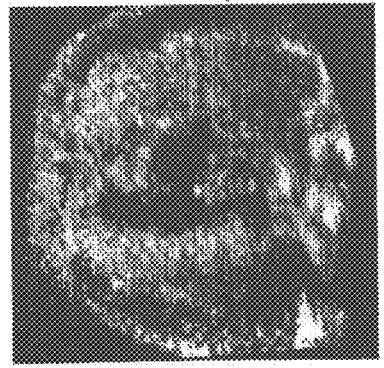
FIG. 12

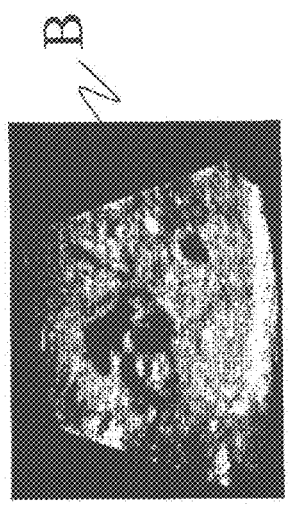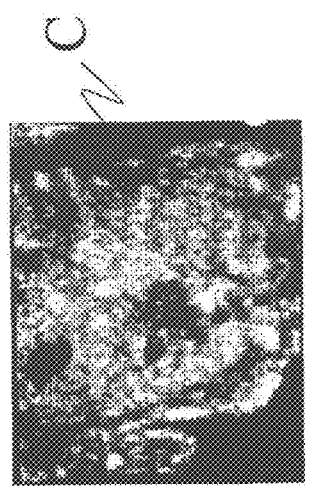
FIG. 13A

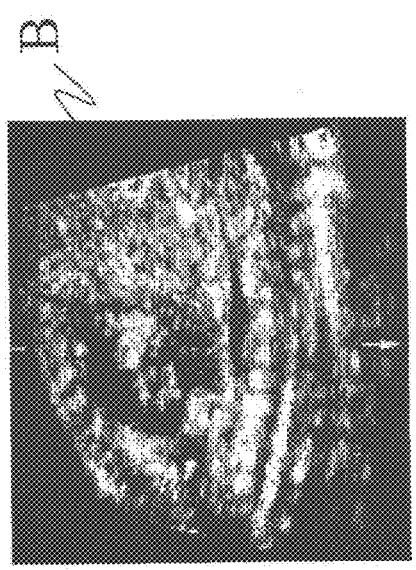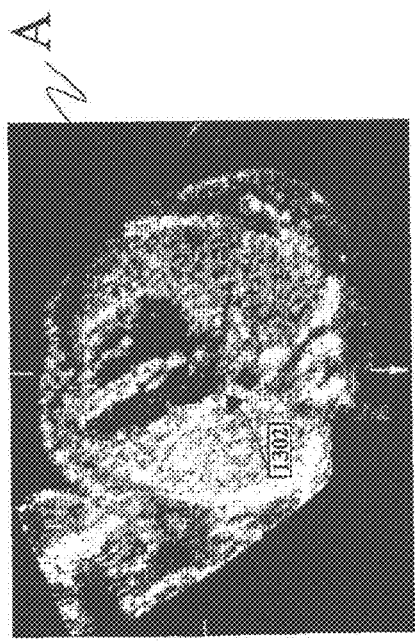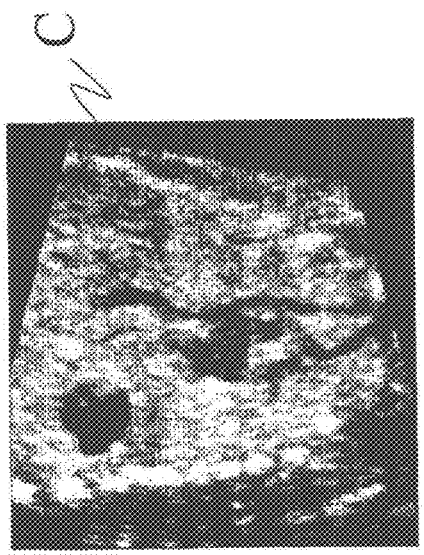
FIG. 13B

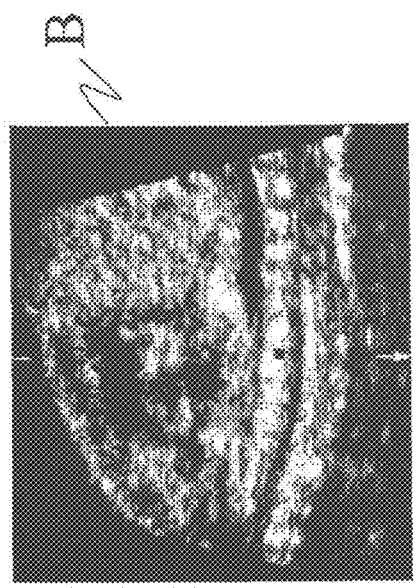
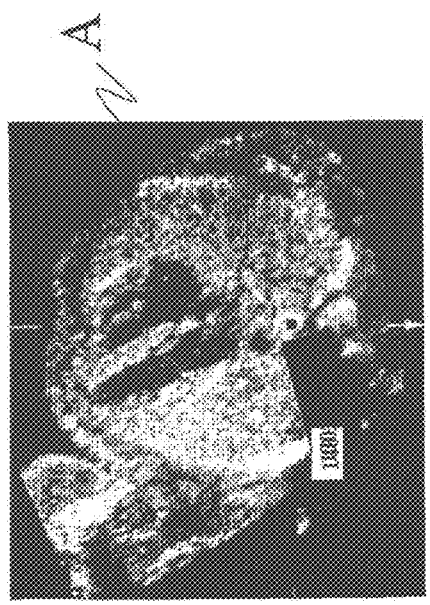
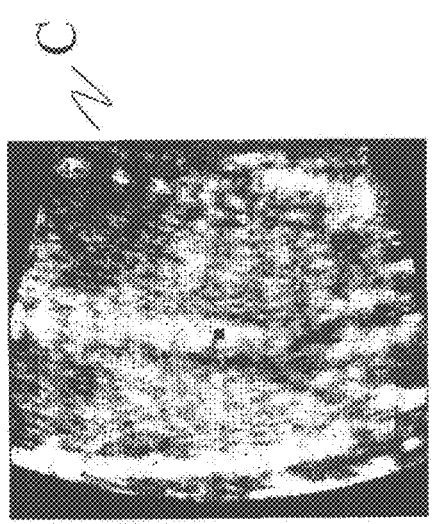
FIG. 14

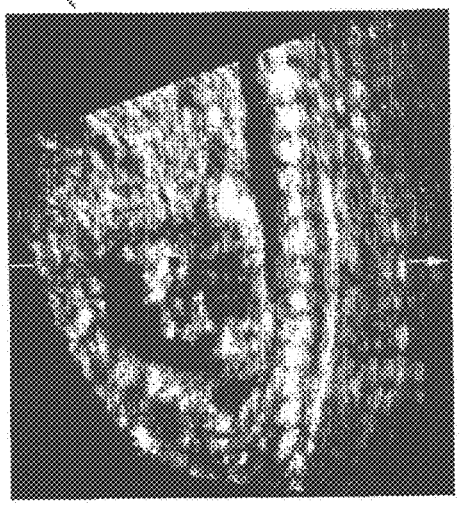
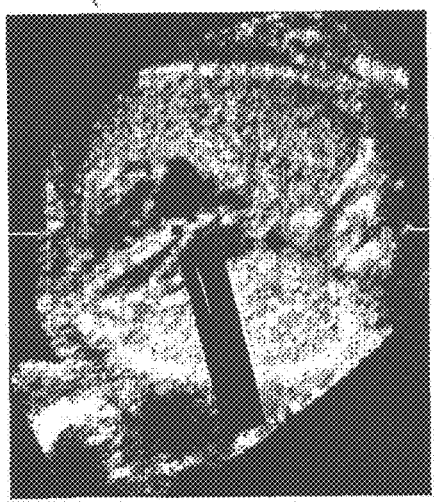
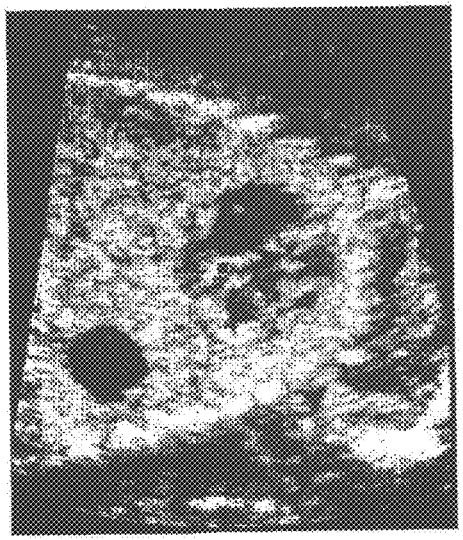
FIG. 16

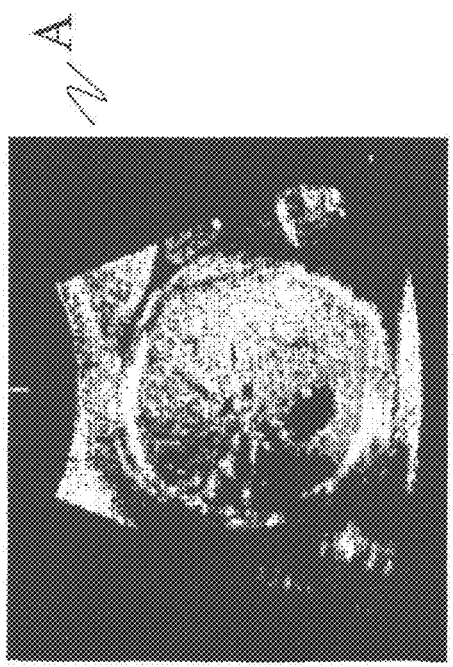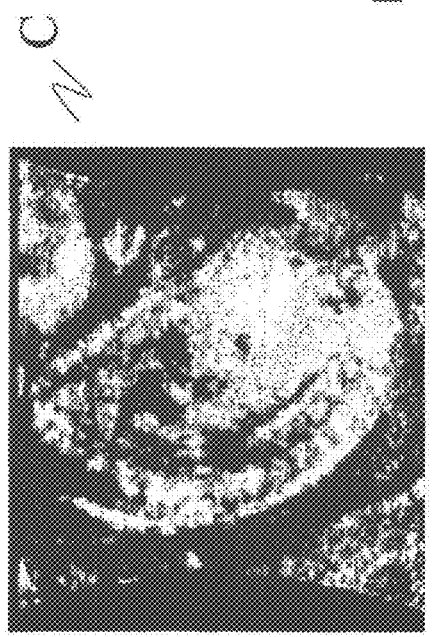
FIG. 18

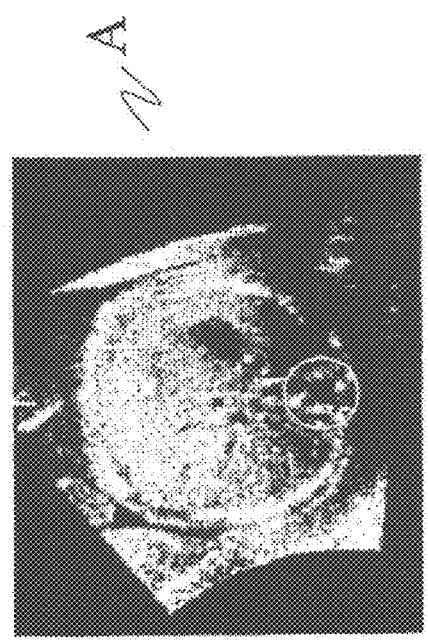
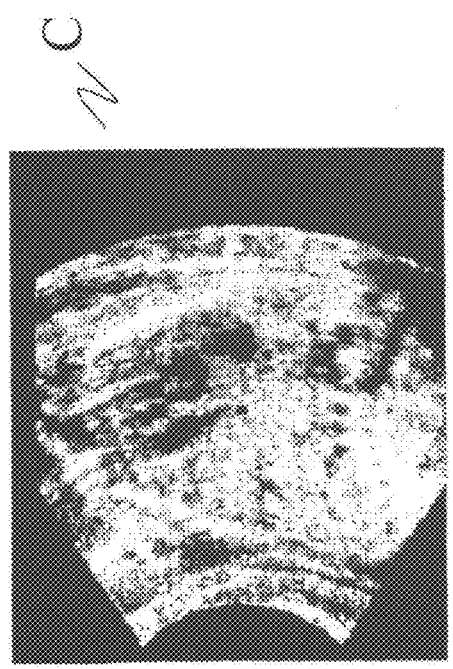
FIG. 19

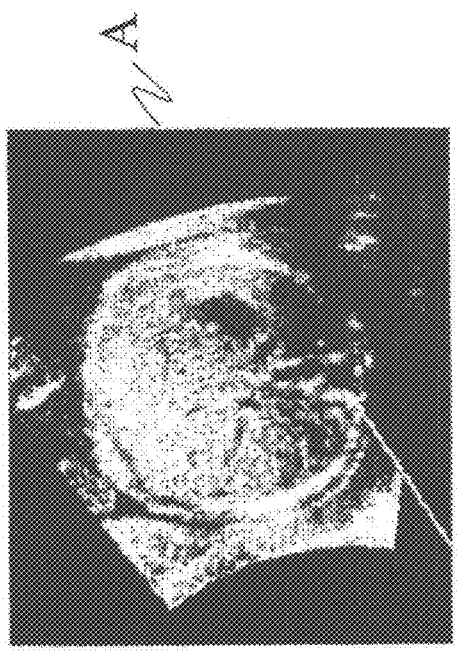
FIG. 20

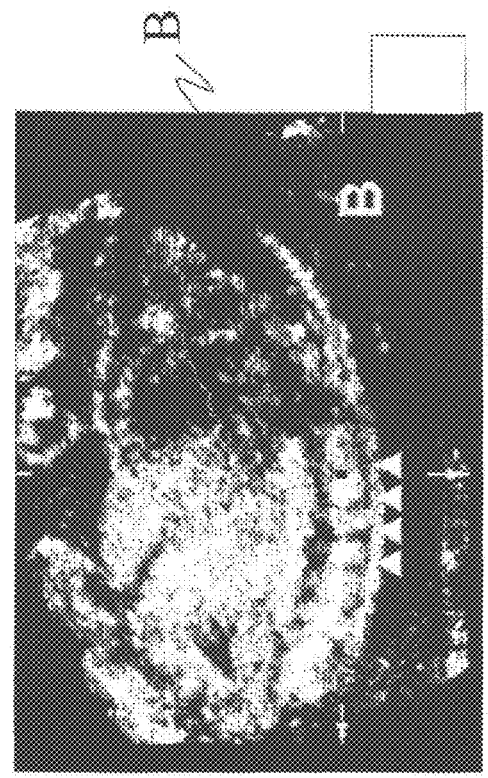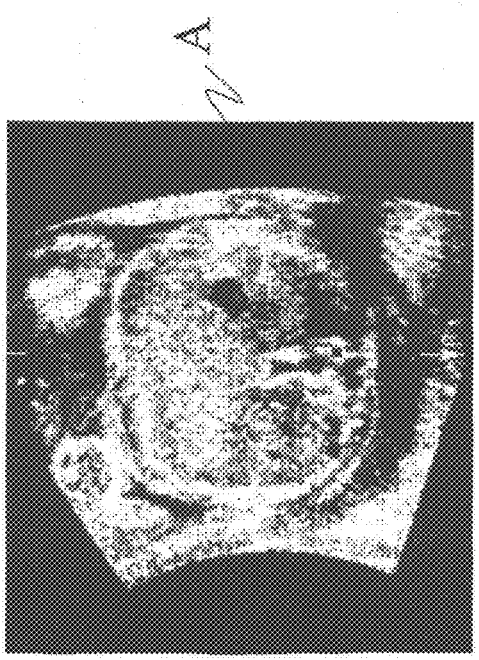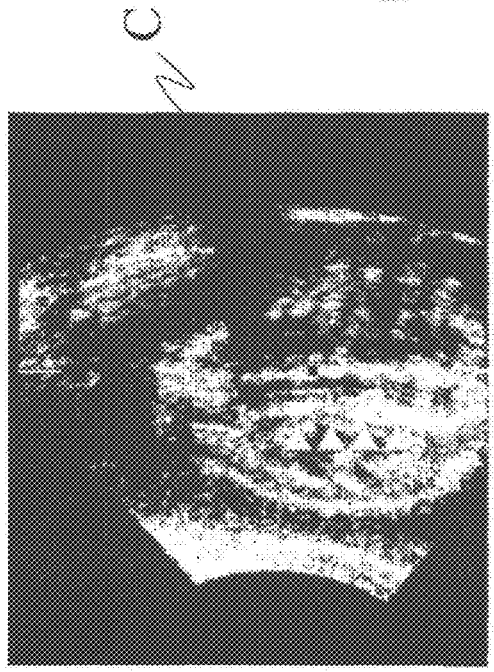
FIG. 21

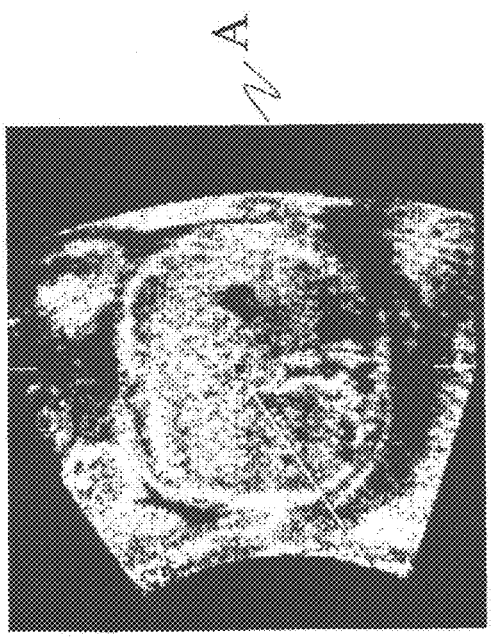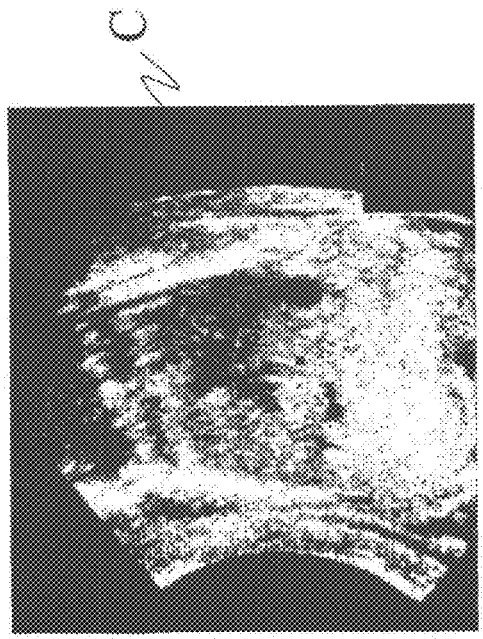
FIG. 22

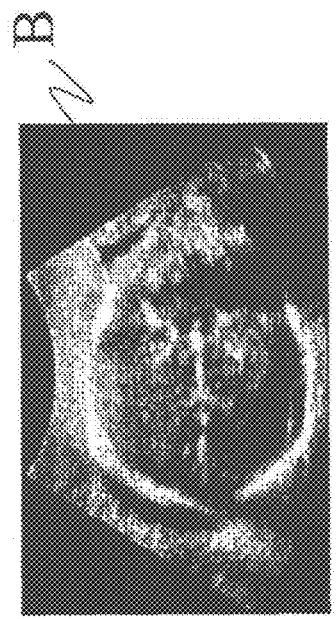
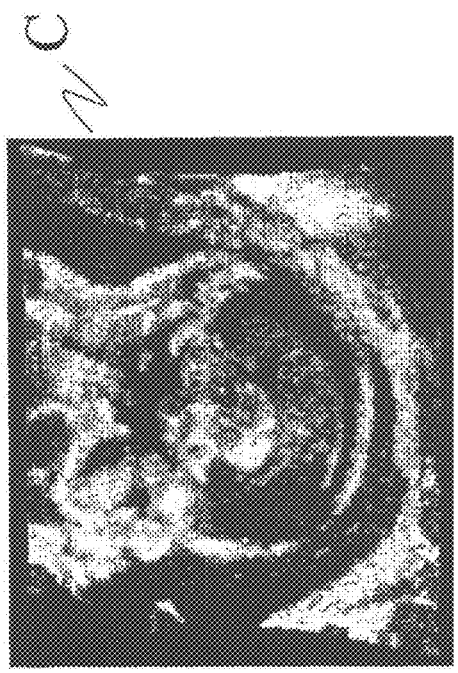
FIG. 24

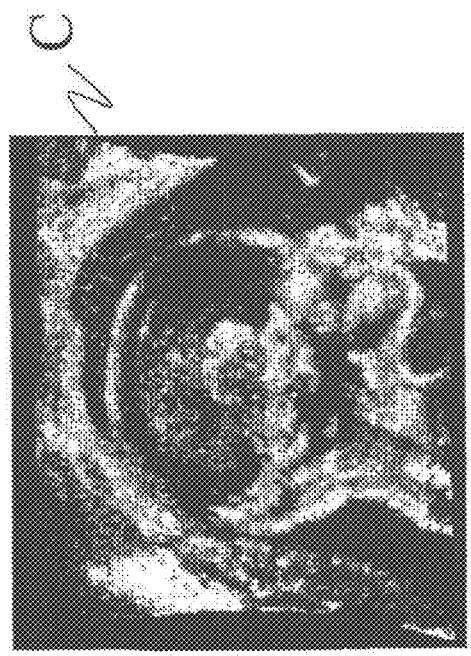
FIG. 25

SYSTEM, METHOD AND MEDIUM FOR ACQUIRING AND GENERATING STANDARDIZED OPERATOR INDEPENDENT ULTRASOUND IMAGES OF FETAL, NEONATAL AND ADULT ORGANS

CROSS-REFERENCE TO RELATED APPLICATIONS

This application claims priority to, and incorporates by reference, Provisional Application Ser. No. 60/463,045, filed Apr. 16, 2003. This application is a continuation-in-part application of Ser. No. 10/823,793, filed Apr. 14, 2004.

DESCRIPTION

Background of the Invention

1. Field of the Invention

The present invention generally relates to acquiring and generating ultrasound still and/or real time images and, more particularly, to acquiring and generating operator-independent displays of ultrasound still and/or real time images of standard anatomic planes of fetal, neonatal and/or adult organs.

2. Background Description

In the art of medical imaging, the development of three-dimensional (3D) and four-dimensional (4D) ultrasonography provides an advance in imaging technology. With 3D ultrasonography, an infinite number of two-dimensional (2D) planes are acquired of (or within) a target volume. The volume acquired by 3D ultrasonography can be displayed on a display monitor by the three orthogonal planes representing the transverse (or axial) (top/bottom), coronal (front/back) and sagittal (left/right) planes of a representative 2D plane within this volume. Such display of an acquired 3D volume by 3 orthogonal planes is known as multiplanar imaging (or multiplanar display).

The multiplanar display of ultrasound volumes enables an operator to manipulate the acquired target volume in order to create and display reconstructed 2D planes within these volumes. For example, in the multiplanar display, the volume can be explored by scrolling through parallel planes in any of the three views, and by rotating the volume to obtain a view of the structures of interest. An operator can thus manipulate the volume data to obtain any desired plane of section after the volume is acquired and the patient is discharged.

Thus, one advantage of 3D ultrasound is the ability to obtain different views from one stored volume. However, even for trained personnel, 3D volume manipulation by the multiplanar display process can be difficult to perform, particularly when the volume involves relatively complex anatomical organs, such as the central nervous system or the heart.

Several studies have documented an added benefit of volume sonography (i.e., 3D sonography) over traditional 2D sonography in fetal imaging. See, e.g., Dyson R. L., Pretorius D. H., Budorick N. E., Johnson D. D., Sklansky M. S., Cantrell C. J., Lai S, Nelson T. R., *Three-Dimensional Ultrasound in the Evaluation of Fetal Anomalies*, Ultrasound Obstetrics Gynecology, 2000; 16:321-328; Merz E., Bahlmann F., Weber G., *Volume Scanning in the Evaluation of Fetal Malformations: A New Dimension in Prenatal Diagnosis*, Ultrasound Obstetrics Gynecology, 1995; 5:222-227; Levaillant R. D., *Two and Three Dimensional Sonographic Assessment of the Fetal Face; A Systematic Analysis of the Normal Face*, Ultrasound Obstetrics Gynecology, 2004; 23:224-231.

However, despite its advantages, ultrasonography is an operator dependent imaging modality. That is, unlike other imaging techniques such as computed tomography (CT) and magnetic resonance imaging (MRI), the quality of the image (s) provided by ultrasound technology depends directly on the skills of the sonographer and/or the sonologist obtaining the images. Furthermore, in obstetrical ultrasound imaging, the variable position of the fetus within the uterus is an added factor that raises the level of difficulty.

This manual process of generating images in obstetrical sonography results in a lack of standardization, image recognition and consistency of diagnosis. Several population based studies have documented suboptimal detection of fetal abnormalities, especially when complex anatomical organs, such as the fetal heart, are targeted. See, e.g., Ewigman B. G., Crane J. P., Frigoletto F. D., Leferve M. L., Bain R. P., McNellis D., *Effect of Prenatal Ultrasound Screening on Perinatal Outcome*, The RADIUS Study Group, New England Journal of Medicine, 1993; 171:821-827; Todros T., Faggiano F., Chiappa E., Gaglioti P., Mitola B., Sciarrone A., and the gruppo piemontese for prenatal screening of congenital heart disease, *Accuracy of Routine Ultrasonography in Screening for Heart Disease Prenatally*, Prenatal Diagnosis, 1997; 17(10): 901-906; Klein S. K., Cans C., Robert E., Jouk P. S., *Efficacy of Routine Fetal Ultrasound Screening for Congenital Heart Disease in Isere County, France*, Prenatal Diagnosis, 1999; 19:318-322; Buskens E., Grobbee D. E., Frohn-Mulder I. M. E., Stewart P. A., Juttmann R. E., Wladimiroff J. W., Hess J., *Efficacy of Routine Fetal Ultrasound Screening for Congenital Heart Disease in Normal Pregnancy*, Circulation 1996; 94:67-72; Stoll C., Dott A. B., Meyer M. J., Pennerath A., Peter M. O., De Geeter B., *Evaluation of Prenatal Diagnosis of Congenital Heart Disease*, Prenatal Diagnosis, 1998; 18:801-807.

In a recent study designed to assess the value of the American Institute of Ultrasound in Medicine accreditation program, 40% of practices seeking initial accreditation were operating below the minimal published guidelines for the performance of ultrasound examination in obstetrics. See, e.g., Abuhamad A. Z., Benacerraf B. R., Woletz P., Burke B. L., *The Accreditation of Ultrasound Practices: Impact on Compliance with Minimum Performance Guidelines*, Journal of Ultrasound Medicine, 2004; 23:1023-1029.

Thus, despite the advantages that volume sonography may provide, significant limitations still exist in volume sonography today. The acquisition, display and manipulation of 3D volumes require a substantial learning curve. Volume sonography in obstetrics is still hampered by the lack of uniformity due to the variable position of the fetus within the uterus and by the technical skills needed to retrieve diagnostic 2D planes out of a 3D volume. These difficulties are compounded for 3D volumes involving anatomically complex organs such as the fetal brain and/or heart. The lack of standardization in the acquisition and display of 3D volumes is an impediment to training.

In order to attain the ease of display and reproducibility of images provided by computed tomography and magnetic resonance imaging, I have discovered that it would be advantageous to standardize the acquisition and display of 3D volumes obtained in volume sonography. I have further discovered that by standardizing the approach to 3D volume acquisition and display and by introducing automation into volume sonography, limitations currently inherent to traditional 2D sonography can be minimized. More particularly, I have discovered that standardization of the manner in which 3D volumes are acquired and displayed can be used to develop methods to facilitate and automate retrieval of diagnostic 2D planes out of a 3D volume.

SUMMARY OF THE INVENTION

It is a feature and advantage of the present invention to provide a system, method and medium that can be used to acquire and generate standardized operator independent ultrasound images of fetal, neonatal and/or adult organs.

It is still another feature and advantage of the present invention to provide a system, method and medium that can be used to acquire and generate standardized operator independent ultrasound images of standard anatomic planes of fetal, neonatal and/or adult organs that can be used to detect normal and/or abnormal imaging relationships within the organ.

It is yet another feature and advantage of the present invention to provide a system, method and medium that can be used to improve the efficiency and diagnostic capabilities of current ultrasound examinations of fetal, neonatal and/or adult organs.

It is a further feature of the present invention to facilitate sonography-related teaching and education, and facilitate training of various medical personnel.

At least one embodiment of the present invention can utilize, for example, a computer program in conjunction with, for example, a general purpose computer and/or standard sonography equipment to obtain and optionally display 2D, 3D and/or 4D ultrasound images. In addition, at least one embodiment of the present invention can provide a medical evaluation or diagnosis of aspects of fetal, neonatal and adult organs (e.g., the fetal heart).

In an exemplary method in accordance with the present invention, a reference plane is obtained for a particular body organ, which can be used as a baseline from which to obtain other planes of interest, such as the four-chamber view plane of the fetal heart. The reference plane can optionally be a standard representative plane that is relatively easy to obtain on 2D ultrasonography, such as the four-chamber view plane of the fetal heart. Exemplary reference planes for the fetal head are the axial biparietal diameter, the axial posterior fossa, the axial lateral ventricles, and the coronal corpus callosum.

A 3D ultrasound imaging apparatus can then be used to acquire a volume of tissue starting, for example, from the level of (or with respect to) the reference plane. The multiplanar display of this acquired volume shows the reference plane in one of the three displayed orthogonal planes, typically in the A plane (current standard 3D acquisition). In accordance with at least one embodiment of the present invention, the spatial mathematical relationship of standardized planes in relation to the reference plane are provided for various fetal, neonatal and adult organs. Software and/or hardware utilized by a general purpose computer and/or standard sonography equipment may then utilize one or more of the mathematical relationships, optionally automatically, to display one or more of the standardized planes. In at least one embodiment of the invention, all standardized planes of interest for a particular body organ may be displayed. Further, either a multiplanar display (where one view of the three-plane multiplanar display is a standardized plane), or a display that shows only one or more standardized planes (without any non-standardized planes that may be part of the multiplanar view), may be provided. As transducer and/or processing capability permit, at least one embodiment of the invention can automatically display one or more standardized planes for a body organ in real time (or substantially in real time), thus bypassing the multiplanar display upon obtaining a scanned volume for the body part.

Advantageously, the constant anatomic relationship of these standardized planes to each other will allow the standardized planes to be used on any patient. In the case of fetal organs, slight modification with regard to the gestational age of the fetus may be utilized to facilitate display. The process of displaying all standardized planes of a particular organ is an operator-independent method of evaluating the organ by ultrasound. In at least one embodiment of the invention, the operator also has the option of viewing a real time display of the standardized planes that are automatically generated.

In at least one embodiment of the present invention, computerized diagnostic capabilities can be used to evaluate images associated with one or more of the standardized planes. For example, imaging software can be utilized to recognize a specific structure within an image (representing, e.g., a portion of the fetal heart), compare the image to a reference image, and identify, for example, normal and abnormal anatomical structures and/or portions thereof. Imaging software for the fetal heart can recognize, for example, in one or more planes, the size of the ventricles and/or the outflow tracts, blood flow across various valves within the heart, and generate indicia (e.g., a report) of normal and abnormal relationships. In addition, imaging software can also be used to adjust plane levels to ensure that an optimum or suitable plane is displayed, which may help standardize the volumes, thus reducing error.

Embodiments of the system, method and medium in accordance with the present invention can provide an image segmentation capability, and orientation tools such as point-to-point references between 2D and 3D images that make images easier to interpret and/or enable, for example, diagnostic information to be easily and clearly conveyed to referring physicians and patients. In addition, embodiments of the system, method and medium in accordance with the present invention can provide, for example, volume and weight estimations of the fetus that are based on 3D volumes (not just 2D planes).

The present invention thus advantageously and generally improves the diagnostic acumen of ultrasound imaging by both standardizing images and automating retrieval of images, thus substantially reducing or eliminating the possibility of human error. By substantially reducing or eliminating the impact of the operator, the present invention also improves the efficiency of ultrasound imaging by reducing the time needed to complete an ultrasound examination, thereby resulting in increased throughput and efficiency of ultrasound laboratories.

Embodiments of the present invention are also directed to standardizing the acquisition and display for the fetal head, chest and abdomen. Ensuring proper orientation of the transducer in acquiring 3D ultrasound volumes is required for successful standardization. Volume standardization in 3D sonography needs to be applied at the level of volume acquisition and display. Standardized acquisition parameters for specific anatomic regions will ensure that the fastest and most uniform acquisition is obtained thus minimizing artifact especially when dealing with fetal movement or motion within an organ such as the fetal heart. Standardization in acquisition of volumes should address the reference plane of acquisition, the size of the acquisition box and the angle of acquisition of a specific target anatomic region.

For instance, the acquisition of a volume of the fetal chest can be standardized by setting the acquisition reference plane at the level of the four-chamber view in an axial view of the chest. The borders of the acquisition box can be placed just outside the fetal skin, and the angle of acquisition can be wide enough to ensure inclusion of the stomach inferiorly and the lower neck superiorly.

More particularly, in one embodiment of the invention, a method for utilizing sonography equipment to acquire and display an ultrasound image of an organ includes moving an ultrasonic transducer to obtain an ultrasound image of a reference anatomic plane of the organ, and using at least one predetermined mathematical relationship to automatically retrieve and respectively display at least one anatomic plane of the organ. If the organ is a fetal heart, the anatomic plane can include at least one of a pulmonary artery, a three vessel view, a left ventricular outflow tract, a ductal arch, a venous connection, and an aortic arch. When acquiring the image, at least two opposing sides of an acquisition box boundaries can be respectively placed just outside a surface and a second surface of fetal skin so that at least one rib of the fetus appears on each of the opposing sides. The acquisition box can be opened so the fetal heart is contained within the box. The acquisition angle should be sufficiently wide so the image includes a view of the stomach inferiorly and the lower neck superiorly.

In another embodiment of the present invention, a method for utilizing sonography equipment to acquire and display an ultrasound image of a fetal heart is provided. The method includes using a device associated with an ultrasonic system to rotate an image in a transverse plane of a four-chamber view of a fetal heart about a Z-axis of a coordinate system in which an X-axis is a horizontal axis, a Y-axis is a vertical axis, and the Z-axis points in a perpendicular direction with respect to a plane defined by the X-axis and the Y-axis, so a spine of the fetus is in a substantially 6 o'clock position, and an apex of the heart is in a left upper quadrant. The device is used to move a reference point in the transverse plane to the spine, thereby bringing a longitudinal view of the spine in a sagittal view, and a vertical view of the spine in a coronal view. The device is also used to rotate the image in the coronal view about the Z-axis until a section of a mid-thoracic spine is aligned substantially vertically in a coronal plane, and a section of the mid-thoracic spine posterior to the heart is aligned substantially horizontally in a sagittal plane. The device is then used to position the reference point in the transverse plane at a crux of the heart, at the level of the insertion of the medial leaflet of the tricuspid valve into the septum. Finally, a predetermined mathematical relationship can be used to automatically retrieve and display one or more planes of interest of the fetal heart. If the fetus is in a breech presentation, the volume is rotated approximately 180 degrees about the Y-axis prior to performing the method.

In another embodiment of the present invention, a method for utilizing sonography equipment to acquire and display an ultrasound image of a fetal abdomen is provided. The method includes moving an ultrasonic transducer to obtain an ultrasound image of an axial view of a fetal abdomen at a level of a plane of an abdominal circumference, opening an acquisition box of the image so the fetal abdomen is contained within the box, utilizing an acquisition angle sufficiently wide so the image includes a view of a sacrum inferiorly and a diaphragm superiorly, and using a predetermined mathematical relationship to automatically retrieve and display one or more planes of interest of the fetal abdomen. At least one rib of the fetus preferably appears on opposing sides of the image. In addition, at least two opposing sides of the box boundaries can be respectively placed just outside a surface and a second surface of fetal skin.

In still another embodiment of the present invention, a method for displaying a volumetric scan of a fetal abdomen is provided. A device associated with an ultrasonic system is used to rotate an image in an abdominal circumference about a Z-axis of a coordinate system in which an X-axis is a horizontal axis, a Y-axis is a vertical axis, and the Z-axis points in a perpendicular direction with respect to a plane defined by the X-axis and the Y-axis, so a spine of the fetus is in a substantially 6 o'clock direction, and a stomach is in the left abdomen. The device is used to move a reference point in the transverse plane to the spine, thereby bringing a horizontal view of the spine in a sagittal plane, and a vertical view of the spine in a coronal plane. The device is also used to rotate the image in the coronal view about the Z-axis until a section of the mid-lumbar spine is aligned substantially vertically in a coronal plane and substantially horizontally in a sagittal plane. Finally, the device can be used to position the reference point in the transverse plane at a center of the fetal abdomen. A predetermined mathematical relationship can then be used to automatically retrieve and display one or more planes of interest of the fetal abdomen. If the fetus is in a breech presentation, the volume is rotated approximately 180 degrees about the Y-axis prior to performing the method.

In another embodiment of the present invention, a method for utilizing sonography equipment to acquire and display an ultrasound image of a fetal head is provided. The method includes moving an ultrasonic transducer to obtain an ultrasound image of an axial view of a fetal head at a level of a plane of a level of lateral ventricles, opening an acquisition box of the image so the fetal head is contained within the box, utilizing an acquisition angle sufficiently wide so the image includes a view of an upper spine inferiorly and a top of the fetal head superiorly, and using a predetermined mathematical relationship to automatically retrieve and display one or more planes of interest of the fetal head. At least two opposing sides of the box boundaries can be respectively placed just outside a first surface and a second surface of the fetal skull.

Yet another method in accordance with the present invention can be used to display a volumetric scan of a fetal head. The method includes using a device associated with an ultrasonic system to rotate an image including lateral ventricles about a Z-axis of a coordinate system in which an X-axis is a horizontal axis, a Y-axis is a vertical axis, and the Z-axis points in a perpendicular direction with respect to a plane defined by the X-axis and the Y-axis, so an inter-hemispheric fissure is aligned substantially horizontally and a frontal portion of a fetal brain is positioned at a right portion of the image with respect to an observer's viewpoint. The device is also used to rotate the image in a sagittal plane about the Z-axis until a fetal face is in a military position. In addition, the device is used to rotate the image in a coronal plane about the Z-axis until an inter-hemispheric fissure is aligned substantially horizontally, and to position a reference point at a midpoint of the inter-hemispheric fissure. A predetermined mathematical relationship can be used to automatically retrieve and display one or more planes of interest of the fetal head. The volume is rotated approximately 180 degrees about the Y-axis prior to performing the method when the fetus is in a cephalic presentation.

There has thus been outlined, rather broadly, the features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

Other features of the present invention will be evident to those of ordinary skill, particularly upon consideration of the following detailed description of the preferred embodiments.

BRIEF DESCRIPTION OF THE DRAWINGS

FIG. 3 shows a plurality of exemplary standard planes of a fetal heart that can be generated.

FIG. 4D represents the distance in millimeters, and FIG. 4E represents the rotation along the Y-axis in degrees.

FIG. 4G represents the rotation about the Y-axis, and FIG. 4H represents the distance in millimeters.

FIG. 5 shows an exemplary 3D multiplanar imaging of a volume of the fetal heart at approximately 20 weeks of gestation, where plane A represents the four-chamber view.

FIG. 6 shows an exemplary 3D multiplanar imaging of a volume of the fetal heart at approximately 20 weeks of gestation, where plane A represents the right ventricular outflow tract.

FIG. 12 shows various views that can be generated from a volume of a fetal heart using an alternate scanning technique of standardized transverse views of the fetal abdomen and chest.

FIG. 13A shows an initial multiplanar view of a 3D ultrasound volume of the fetal chest obtained at the level of the four-chamber view, at approximately 19 weeks of gestation.

FIG. 13B shows a 3D volume in FIG. 12A, magnified and standardized in plane A.

FIG. 14 shows how a reference point moved to the spine in plane A brings a longitudinal view of the spine in plane B and a vertical view in plane C.

FIG. 16 shows the reference point moved to the crux of the heart, at the level of the insertion of the tricuspid valve leaflet into the septum, in plane A.

FIG. 18 shows an initial multiplanar view of a 3D ultrasound volume of the fetal abdomen at 20 approximately weeks of gestation.

FIG. 19 shows a 3D volume of FIG. 18, magnified and standardized in plane A.

FIG. 20 shows how a reference point moved to the spine in plane A brings a longitudinal view of the spine in plane B and plane C.

FIG. 21 shows rotation about the Z-axis is applied to planes B and C, and resulting alignment of the lumbar spine horizontally in plane B and vertically in plane C.

FIG. 22 shows the reference point moved to the center of the abdomen in plane A.

FIG. 24 shows an initial 3D ultrasound volume of a fetal head at the level of the lateral ventricles, obtained at approximately 18 weeks of gestation, in a fetus in left occiput cephalic presentation.

FIG. 25 shows the same 3D volume that is displayed in FIG. 24, now rotated about the Y and Z axes in plane A.

DETAILED DESCRIPTION OF EMBODIMENTS OF THE INVENTION

Figure 1:
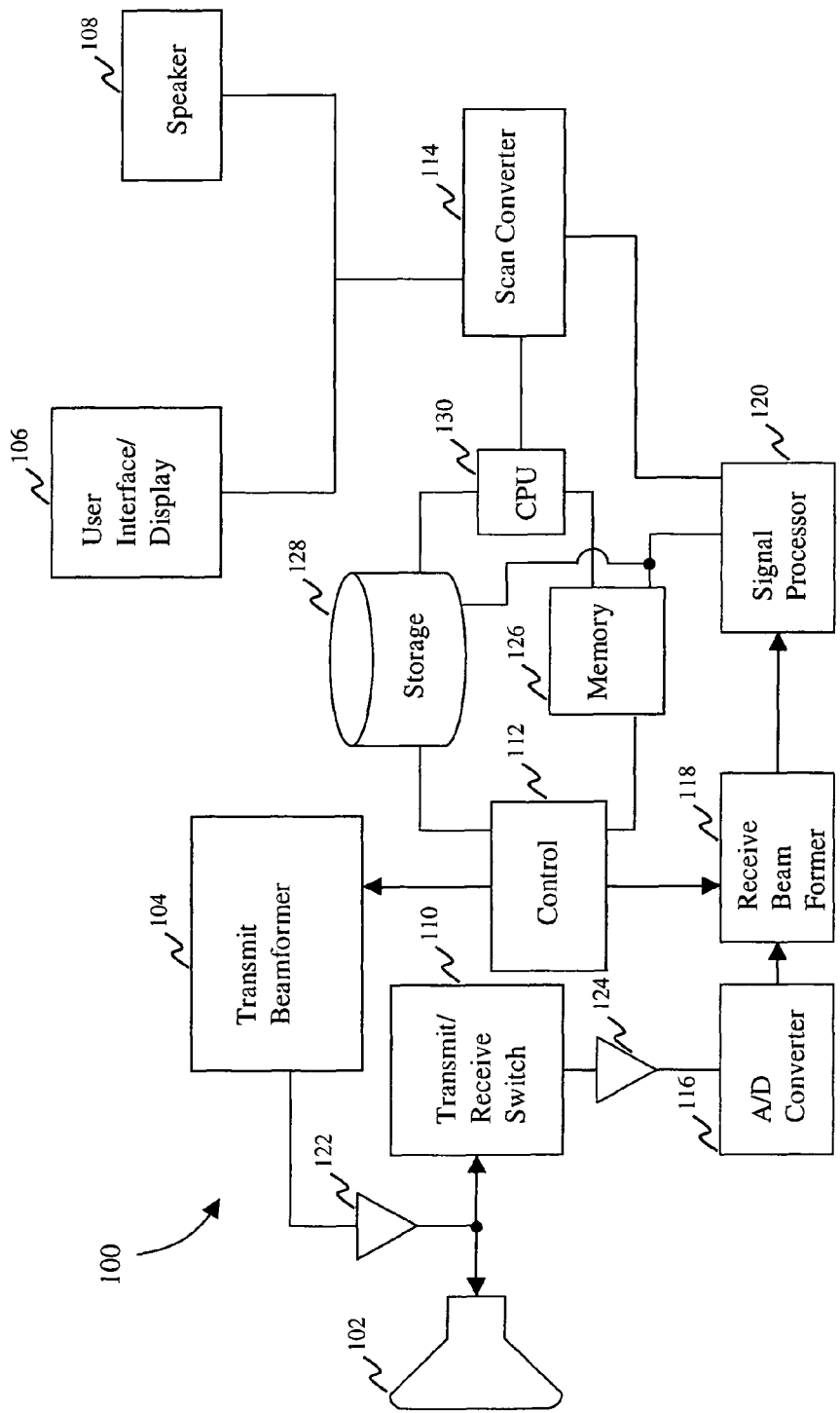
FIG. 1 is a block diagram of an exemplary sonography system that can be used in conjunction with the present invention.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

Two concepts of 3D imaging are pertinent with regard to the present invention. First, the acquired volume of a particular anatomical structure by 3D ultrasonography, such as a volume of the fetal heart, contains all of the anatomical 2D planes for a complete evaluation of this structure in normal and abnormal conditions. Second, for every human organ, the anatomical 2D planes needed to perform a complete anatomical evaluation of a particular organ are organized in a constant anatomic relationship to each other. I have discovered that it is therefore possible to obtain a volume of a specific organ, such as the fetal heart, and utilize an optionally automated software program to display from this volume, one or more 2D planes that facilitate evaluation of the organ. This aspect of the present invention is referred to as Automated Multiplanar Imaging (AMI)/Automated Sonography. I have further discovered ways to standardize the acquisition and display one or more standardized planes for a particular body organ.

FIG. 1, generally at 100, is a block diagram of an exemplary sonography system that can be used in conjunction with one or more embodiments of the present invention. Transducer 102 is used to scan a volume of a patient's body, to obtain an image of the scanned volume. As known in the art, transducer 102 generally includes a plurality of transducer elements that generate focused acoustic signals responsive to signals generated by transmit beamformer 104. Transducer 102 may include sufficient electronics and/or processing capability to provide or facilitate display of one or more standardized planes subsequent to acquisition (e.g., in a real time or near-real time manner) of image data for a particular body organ. The outputs of transport beamformer 104 can be amplified by amplifier 122 prior to reaching transducer 102.

Transmit/receive switch 110, which can utilize, for example, a plurality of diodes, blocks the transmit beamformer 104 voltage pulses from being received at amplifier 124, A/D converter 116, and receive beamformer 118. Transmit/receive switch 110 thus protects receive beamformer 118 from being damaged by transmit beamformer 104 transmission pulses. In operation, when a transmit pulse from transmit beamformer 104 is present, the diodes of transmit/receive switch 110 switch on, thus short circuiting receive beamformer 118 to ground, while presenting a high impedance path to transmit beamformer 104. In at least one alternate embodiment of the invention, transmit/receive switch 110 does not need to be utilized if separate transmit and receive transducers (not shown) are respectively connected to transmit beamformer 104 and receive beamformer 118.

Transducer 102 receives the ultrasound energy from points within the patient's body, generally at different times, and converts the received ultrasound energy to transducer signals which may be amplified by amplifier 124, converted to digital signals by A/D converter 116, and received by receive beamformer 118. In another embodiment, beamformer 118 can operate on analog signals, if A/D converter 116 is not utilized.

Signal processor 120 may operate to process signals received from receive beamformer 118 in accordance with one or more of at least three primary image acquisition modes. First, 2D gray-scale imaging, which is referred to as B-mode. Second, Doppler imaging, which is used for blood flow, and is referred to as F-mode. Third, spectral Doppler imaging, can show blood flow velocities and their frequencies, and is referred to as D-mode. Signal processor 120 generally processes signals received from receive beamformer 118 in a manner that substantially optimizes the signals for output in their selected display mode. Signal processor may also optimize signals for audio output using speaker 108, and store the processed signals in memory 126 and/or storage 128. Memory 126 can be, for example, a random access memory, whereas storage 128 may be a medium such as a standard hard drive and/or CD-ROM.

Scan converter 114 is a standard device that, optionally in conjunction with central processing unit (CPU) 130, changes the scan rate of the signals received from signal processor 120 to a scan rate, such as a standard raster scan rate, that is used by user interface/display 106. Display 106 can optionally provide a user-controlled and operated selector, such as a standard mouse, that allows the user to select one or more planes of interest that can be displayed. The user can optionally select any (or all) standardized planes for a particular body organ to be displayed. In at least one embodiment of the invention, the default mode of operation for system 100 can be to display all standardized planes of interest for a particular body organ, once a reference plane is acquired by system 100. Scan converter 114 can also process signals received from signal processor 114 to that they can audibly be output on speaker 108.

Control system 112 coordinates, for example, operation of transmit beamformer 104, receive beamformer 118, signal processor 120, and related elements of system 100. Memory 126 and storage 128 may be used to store, for example, the software that generates standardized planes of interest in accordance with the present invention, as well as control instructions for controller 112.

Figure 2:
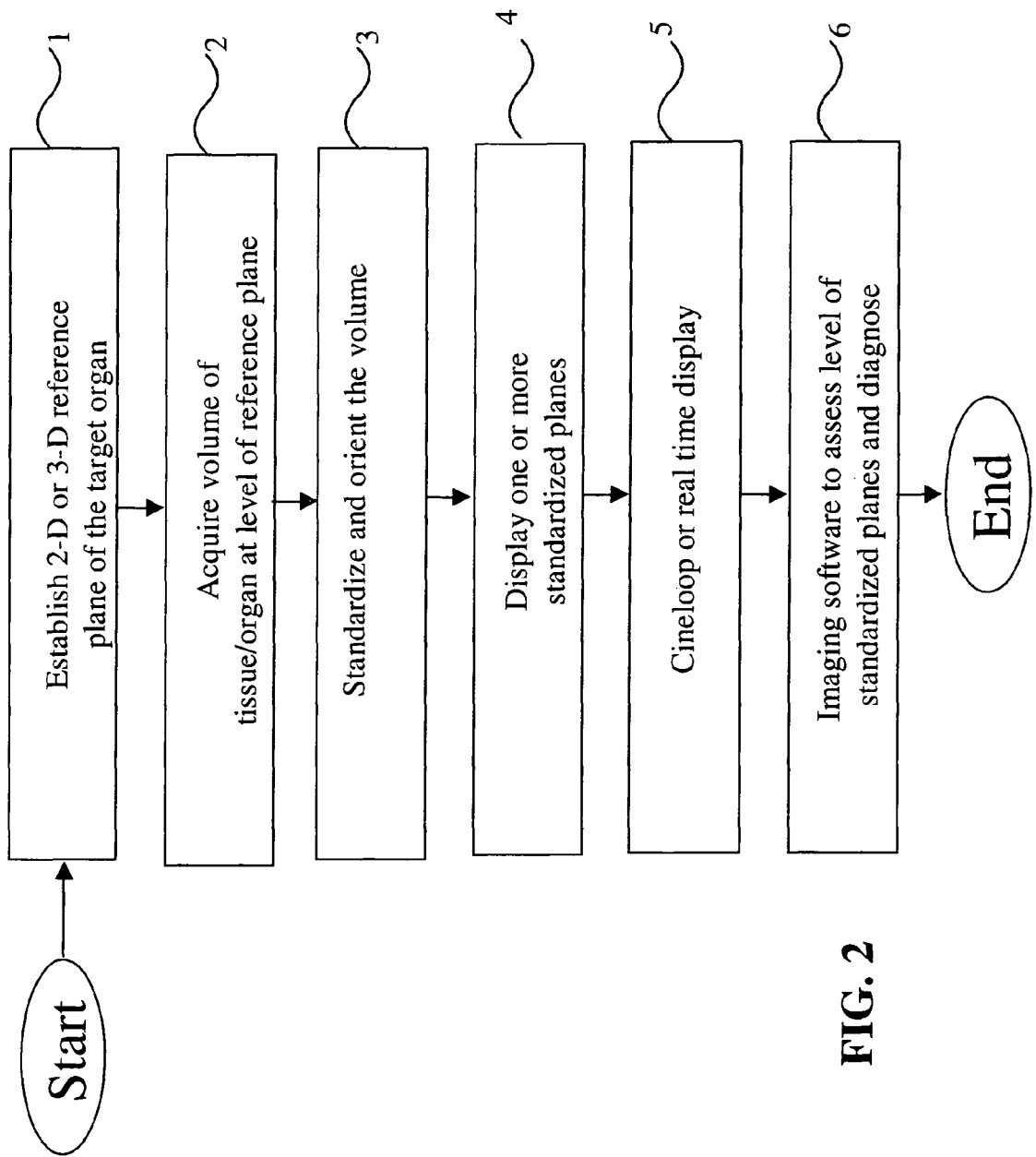
FIG. 2 is a flow diagram of an exemplary method in accordance with the present invention.
Figure 4A:
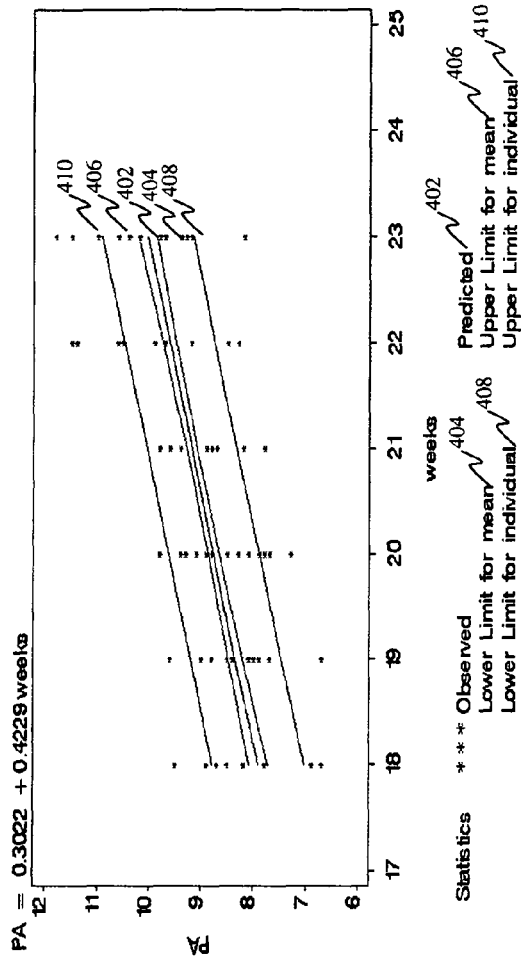
FIG. 4A is a regression model, plot, and associated data for the relationship of the fetal pulmonary artery plane to the four-chamber view plane between approximately 18-23 weeks of gestation.
Figure 4B:
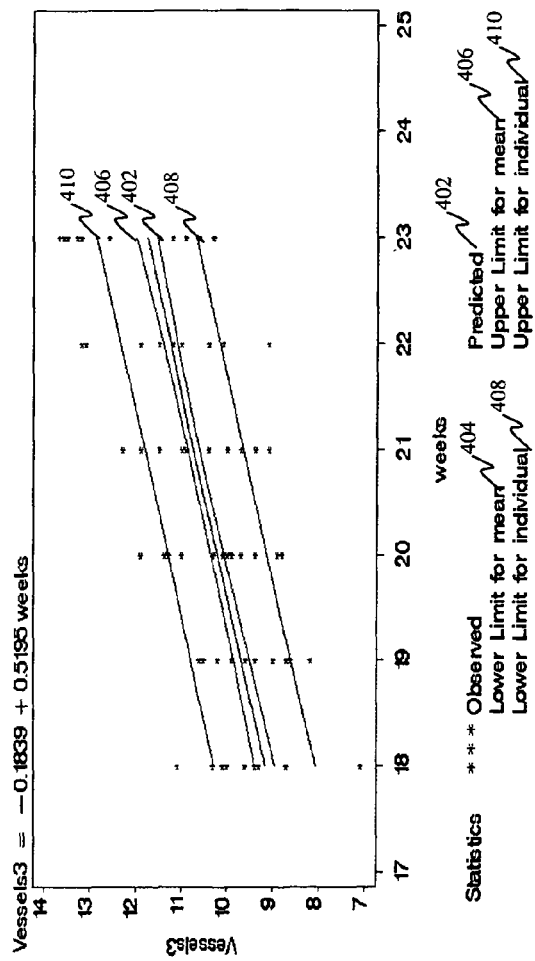
FIG. 4B is a regression model, plot, and associated data for the relationship of the fetal three vessel view plane to the four-chamber view plane between approximately 18-23 weeks of gestation.
Figure 4C:
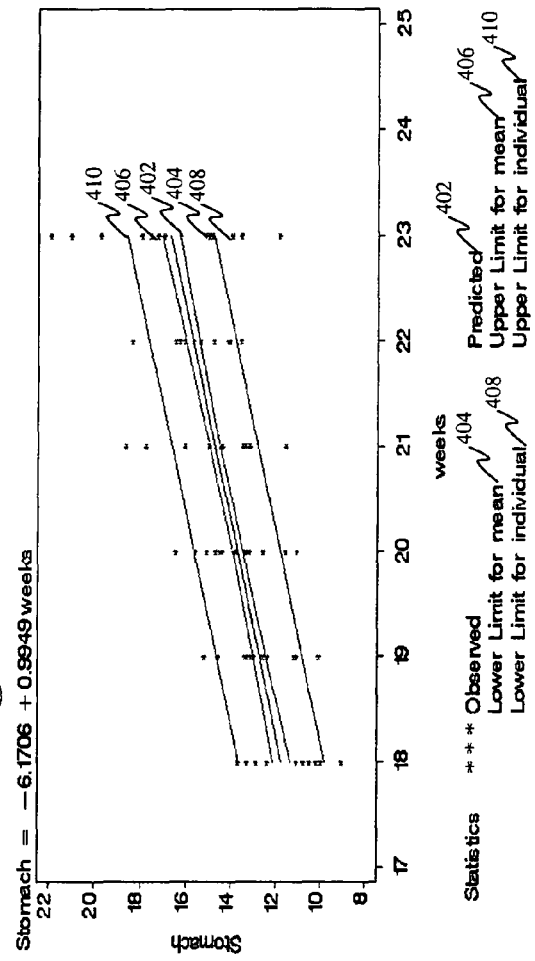
FIG. 4C is a regression model, plot, and associated data for the relationship of the fetal axial stomach plane to the four-chamber view plane between approximately 18-23 weeks of gestation.
Figure 4D:
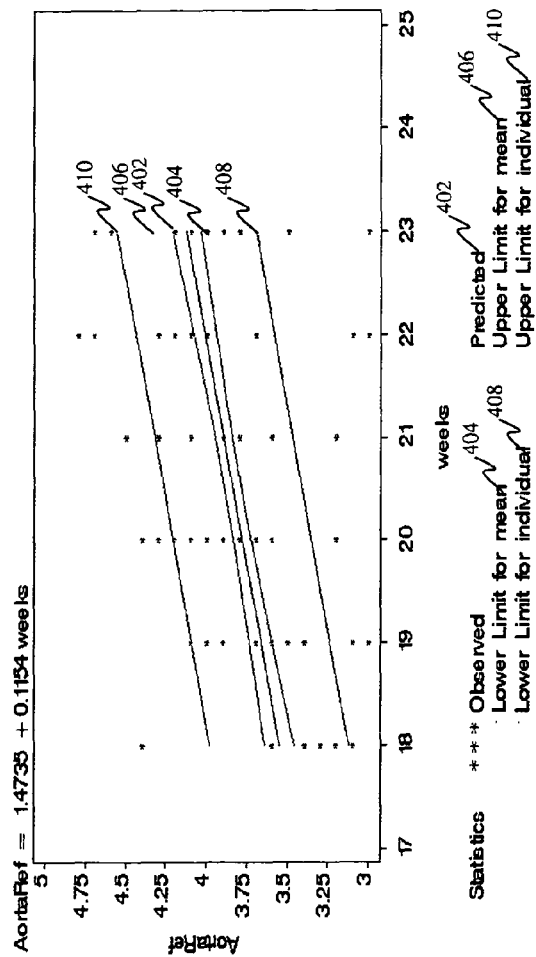
FIGS. 4D and 4E are regression models, plots, and associated data for the relationship of the fetal aorta plane to the four-chamber view plane between approximately 18-23 weeks of gestation.
Figure 4E:
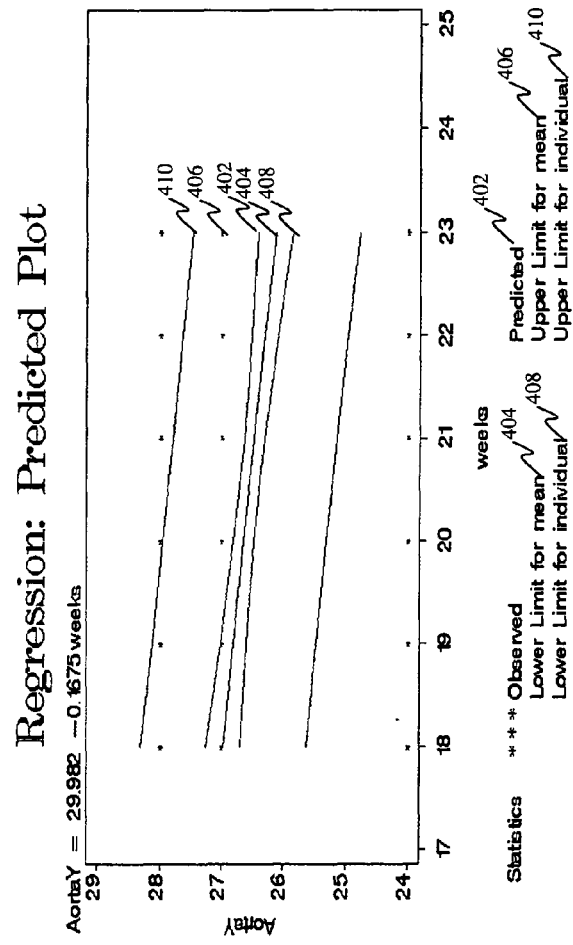
Figure 4F:
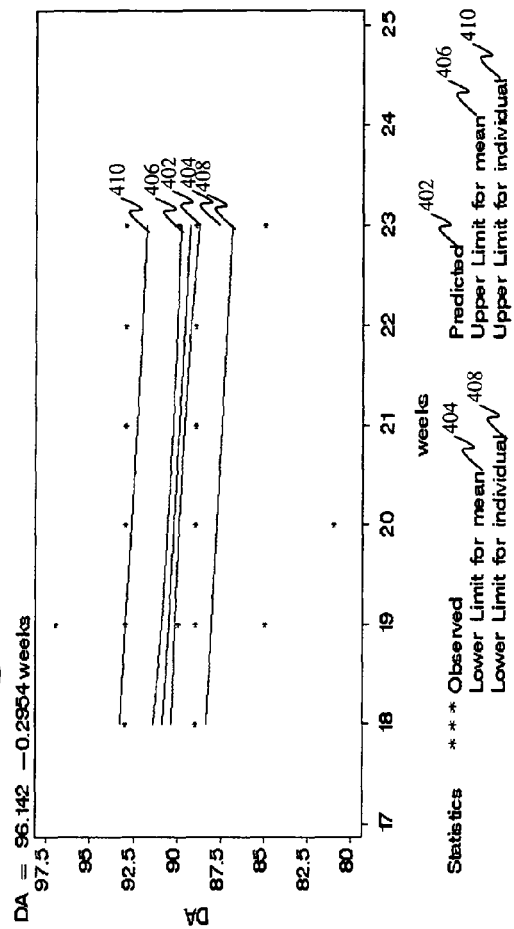
FIG. 4F is a regression model, plot, and associated data for the relationship of the fetal ductus arteriosis to the four-chamber view plane between approximately 18-23 weeks of gestation.
Figure 4G:
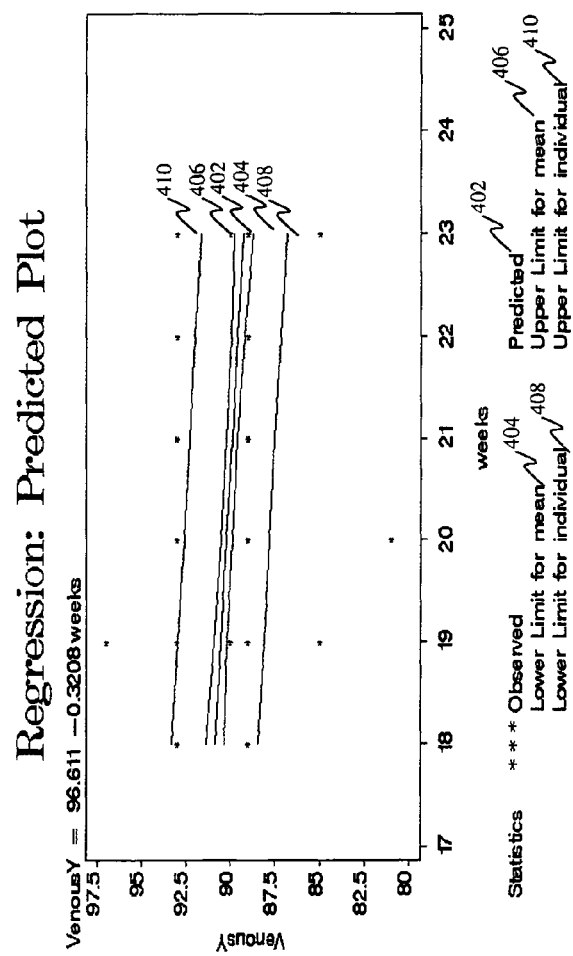
FIGS. 4G and 4H are regression models, plots, and associated data for the relationship of the fetal venuous connection plane to the four-chamber view plane between approximately 18-23 weeks of gestation.
Figure 4H:
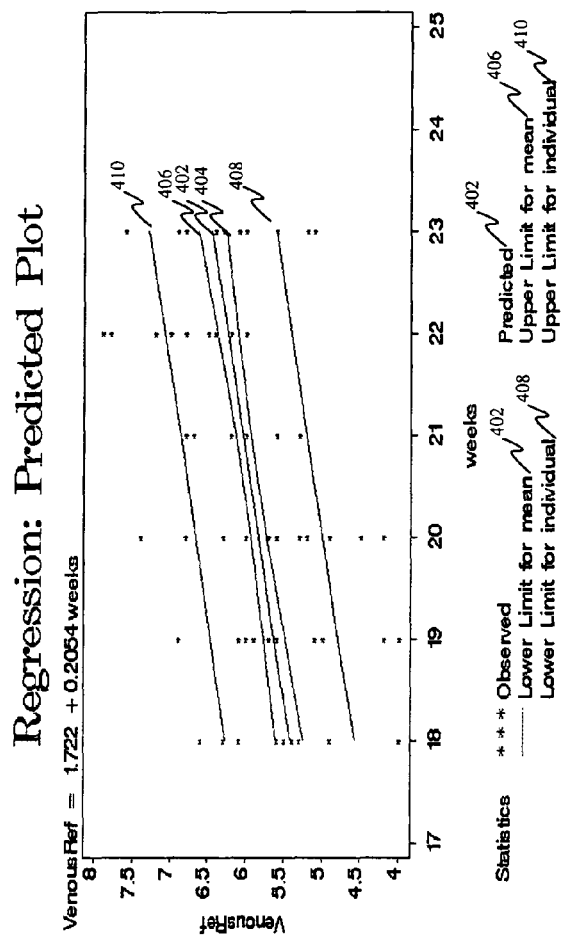
Figure 4I:
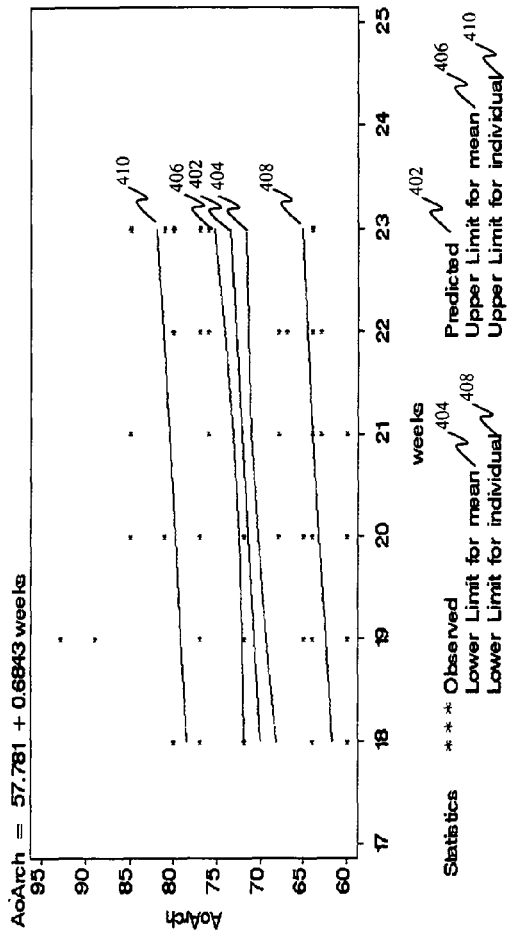
FIG. 4I is a regression model, plot, and associated data for the relationship between the fetal aortic arch plane to the four-chamber view plane between approximately 18-23 weeks of gestation.
Figure 7:
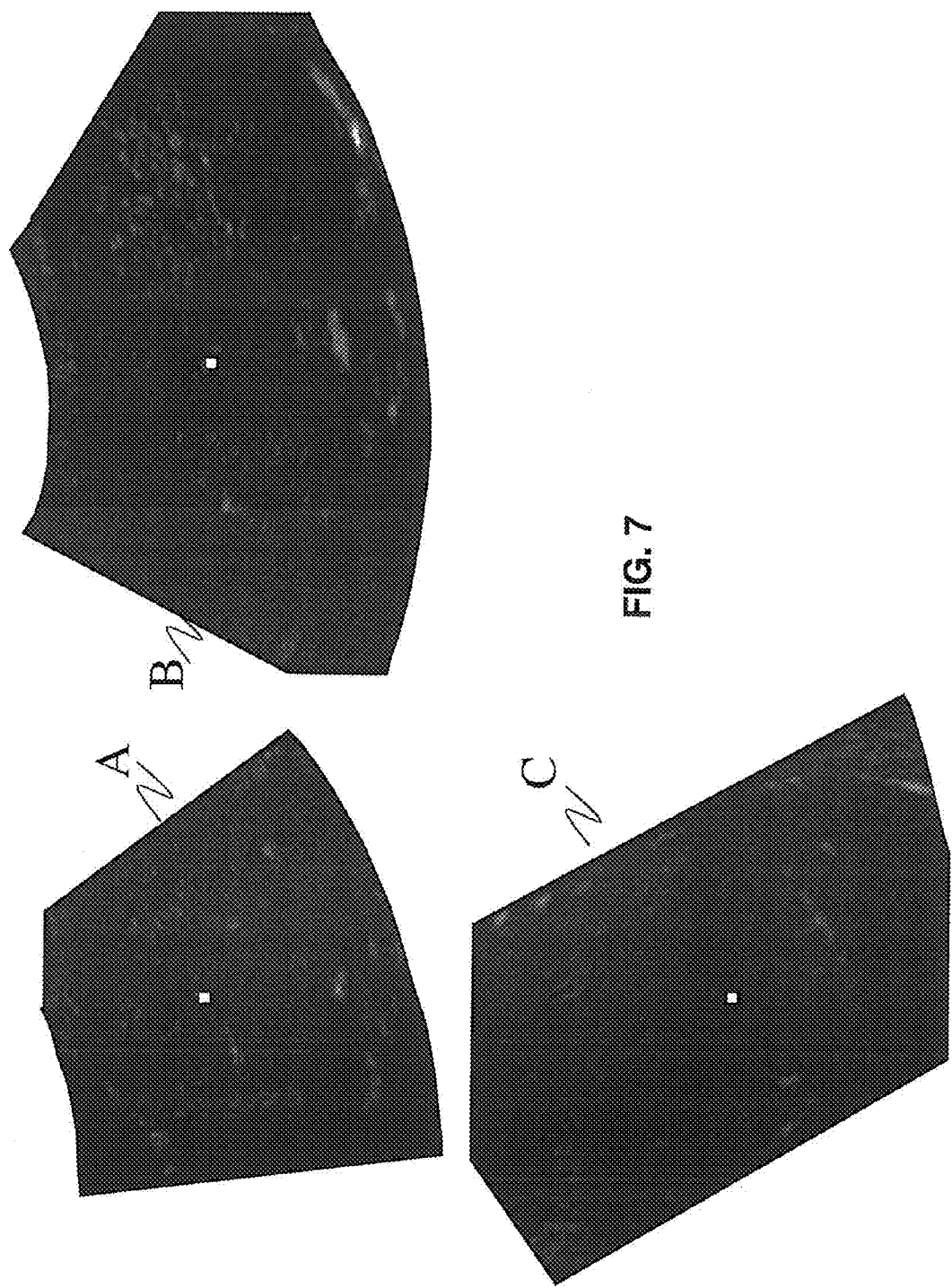
FIG. 7 shows an exemplary 3D multiplanar imaging of a volume of the fetal heart at approximately 20 weeks of gestation, where plane A represents the left ventricular outflow tract.
Figure 8:
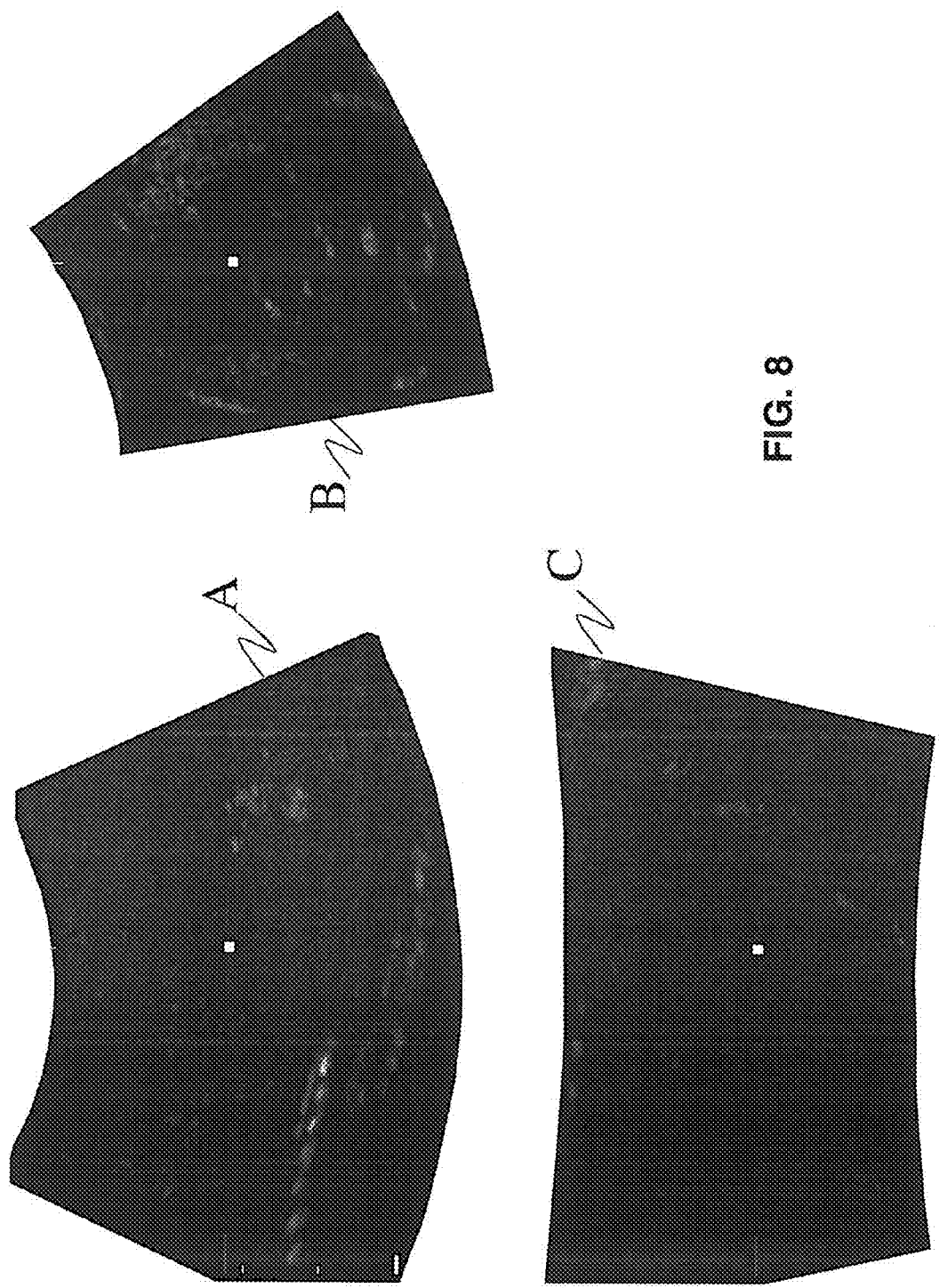
FIG. 8 shows an exemplary 3D multiplanar imaging of a volume of the fetal heart at approximately 20 weeks of gestation, where plane A represents the ductal arch.
Figure 9:
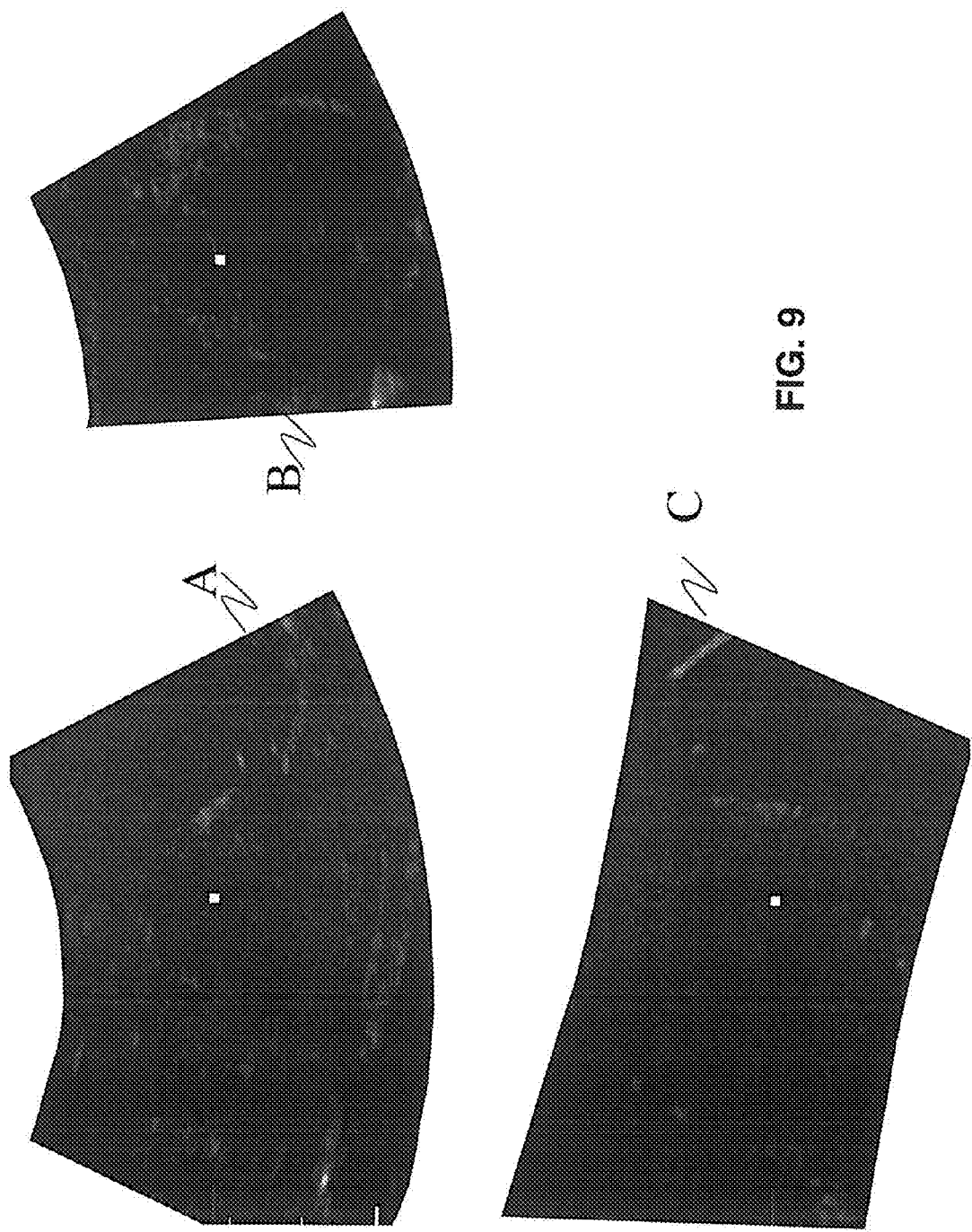
FIG. 9 shows an exemplary 3D multiplanar imaging of a volume of the fetal heart at approximately 20 weeks of gestation, where plane A represents the aortic arch.
Figure 10:
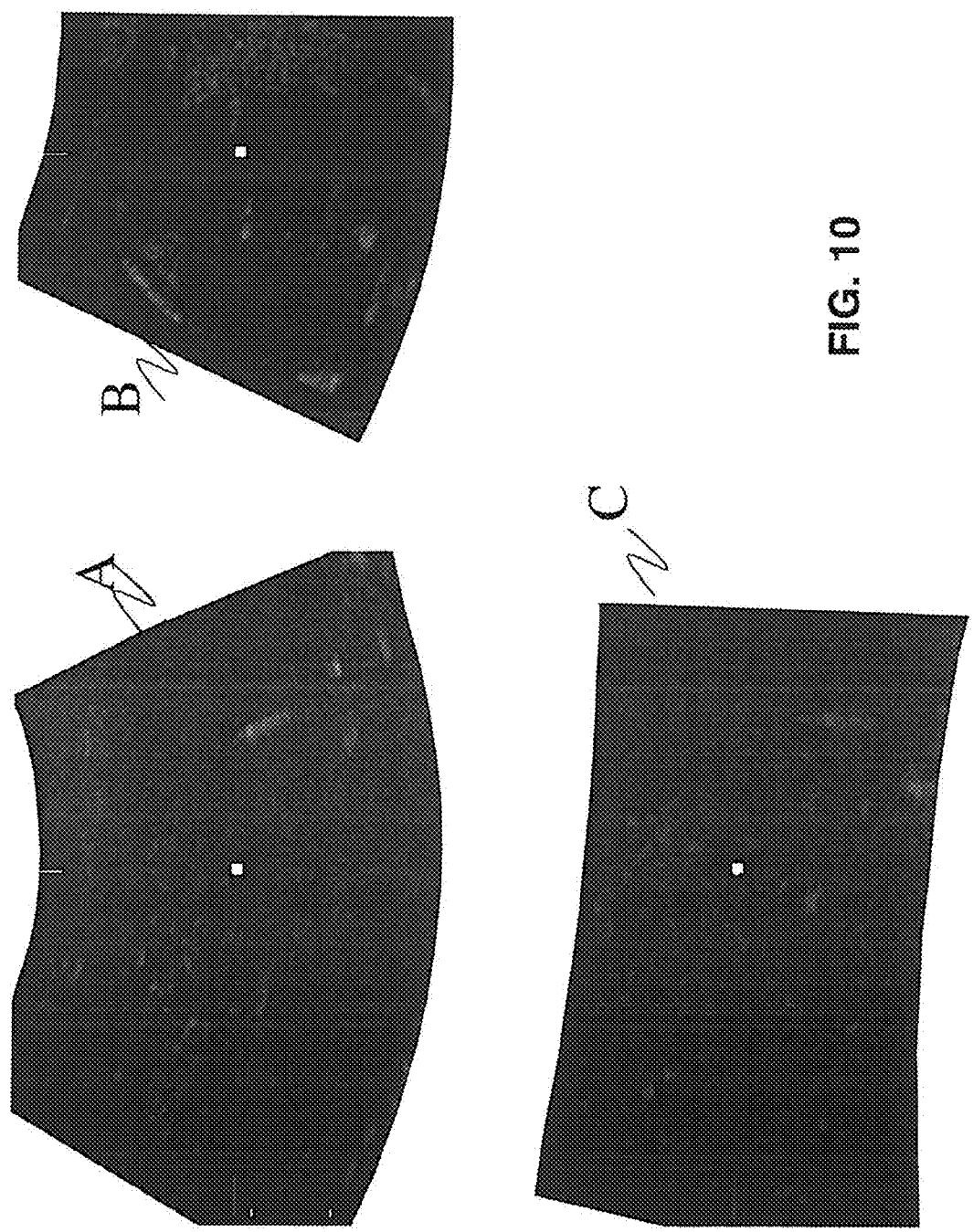
FIG. 10 shows an exemplary 3D multiplanar imaging of a volume of the fetal heart at approximately 20 weeks of gestation, where plane A represents the venous connections.
Figure 11:
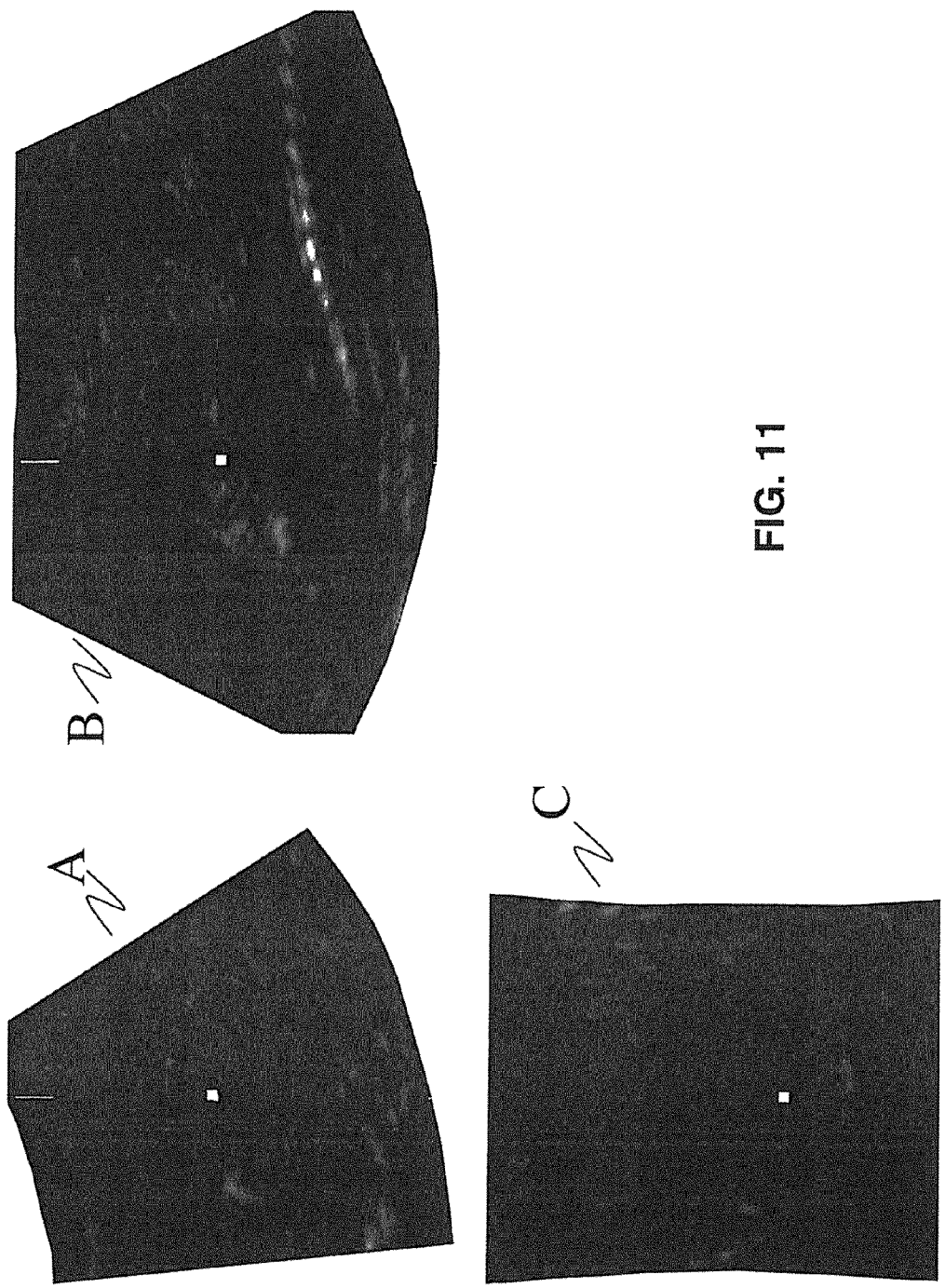
FIG. 11 shows an exemplary 3D multiplanar imaging of a volume of the fetal heart at approximately 20 weeks of gestation, where plane A represents the three vessel view.

Referring now to FIG. 2, an exemplary method in accordance with the present invention is shown. At step 1, a reference plane is typically obtained in a conventional manner by, for example, a sonographer or a sonologist using conventional 2D ultrasonography. The reference plane, which is typically a plane that can be readily obtained by 2D ultrasonography (e.g., four-chamber view of the heart or the lateral ventrical axial plane of the head), can be used as a baseline from which to obtain other planes of interest for a particular organ. A sonography system, such as shown in FIG. 1, can be used to obtain the reference plane. The reference plane can also be obtained directly as a volume by 3D/4D ultrasonography when transducer technology allows. In general, any plane can be used as a reference plane for a particular organ once the mathematical relationships (e.g., trigonometric relationships) for the standardized planes of interest are defined with respect to a known reference plane. Then, if necessary (or desired), the mathematical relationships for the known reference plane can be adjusted or redefined (e.g., recalculated), using standard mathematical techniques and/or operations for an arbitrary reference plane once the coordinates of the arbitrary reference plane are established. Exemplary planes for the fetal heart that can be utilized are as follows:

a. The four-chamber view
b. The right ventricular outflow
c. The left ventricular outflow
d. The ductal arch
e. The aortic arch
f. The venous connections, and
g. The three vessel view Planes d, e, and f referred to above are specific fetal cardiac planes that are not ultrasonographically displayed in the adult heart given the presence of air in the adult lungs and the relative large size of the adult heart compared to the fetal heart.

Referring again to FIG. 2, at step 2, a 3D ultrasound imaging apparatus, such as shown in FIG. 1, can be used to acquire a volume of tissue starting, for example, from the level of the reference plane. The direction of the acquisition is standardized, and in obstetrical imaging is based on the fetal position within the maternal abdomen.

FIG. 3, shows a standard 4-chamber view of a fetal heart 302 that can be used as a reference plane to generate the venous connections view 304, the ductal arch view 306, the left ventricular outflow track 308, the right ventricular outflow track 310, and the aortic arch 312. In another embodiment, one or more of figures 302, 304, 306, 308, 310, 312 can be displayed automatically, subsequent to acquiring the image data. Other standard views for other body organs can also be displayed.

As indicated above, any plane can also be used as a reference plane for the fetal heart, as well as for other organs. For example, a transverse lateral ventrical plane (not shown) can be used as a reference plane of a fetal head.

At step 3 in FIG. 2, the reference plane is fixed and standardized in its orientation within the volume by using standard 3D sonography equipment, such as shown in FIG. 1, to rotate the reference plane into a preset orientation within the volume. For example, the plane of the four-chamber view of the fetal heart 302 can be rotated, using rotation about the Z-axis in a standard coordinate system to place the spine at approximately the 6 o'clock position, and the apex of the heart in the left upper quadrant. Standardization of volume acquisition and display of various organs is discussed in connection with FIGS. 12-27.

At step 4 in FIG. 2, the computerized program that contains the mathematical formulas that relate the reference plane to all the standardized planes for a particular organ (e.g., the fetal heart) is applied to automatically retrieve one or more of the standardized planes from the acquired 3D volume. In the case of the fetal heart, once the computerized program is applied to the 3D volume with the reference plane (e.g., 4 chamber view), any or all planes b-g identified above can be displayed from a single acquisition of the volume as shown in FIG. 3.

Equations (1)-(9) below pertain to a regression model for various planes of interest of a fetal heart in mathematical relation to the four-chamber view plane that is between approximately 18 and 23 weeks of gestation.

$$\text{Pulmonary artery} = -0.0017 + 0.4393 * \text{weeks} \quad (1)$$

$$\text{Three vessel view} = -0.4407 + 0.532 * \text{weeks} \quad (2)$$

$$\text{Axial stomach} = -5.1499 + 0.9426 * \text{weeks} \quad (3)$$

$$\text{Left ventricular outflow tract-ref} = 1.2402 + 0.1268 * \text{weeks} \quad (4)$$

$$\text{Left ventricular outflow track-}Y = 29.772 - 0.1568 * \text{weeks} \quad (5)$$

$$\text{Ductal arch} = 94.313 - 0.2151 * \text{weeks} \quad (6)$$

$$\text{Venous connection-}Y = 94.313 - 0.2151 * \text{weeks} \quad (7)$$

$$\text{Venous connection-ref} = 1.7577 + 0.2047 * \text{weeks} \quad (8)$$

$$\text{Aortic arch} = 53.459 + 0.8727 * \text{weeks} \quad (9)$$

FIGS. 4A-I shows various regression plots and variance data respectively associated with Equations (1)-(9). In the tables shown in FIGS. 4A-I, the predicted value lower confidence level (lcl), upper confidence level (ucl), and standard error are shown for each regression.

Table 1 below describes additional formulas that can be used to generate standard planes of a fetal heart at approximately 20 weeks of gestation, when the reference plane is the four-chamber view. Transverse views without any rotations from the fetal abdomen to the neck may also be used to allow medical personnel to provide an evaluation of the fetal heart. In this case, the fetal heart can be evaluated when a volume is obtained by sliding transducer 102 from the fetal stomach up to the neck.

TABLE 1

| Definition | Shift (mm) |
| --- | --- |
| Abdominal circumference | 13.7 |
| Left ventricular outflow tract (aorta) | 3.8 |
| Right ventricular outflow tract (PA) | 8.7 |
| Three vessel view | 10.2 |

Thus, a view of the left ventricular outflow tract can be obtained by shifting a plane 3.8 mm from (e.g., away from the stomach) and parallel with the four-chamber view. In addition, an axial view of the abdomen at the level of the stomach can be obtained by shifting the plane 13.7 mm from the four-chamber view. Note that since the three planes of Table 1 are each transverse planes (i.e., parallel to the four-chamber view), only distance (in mm) is utilized, and rotation about any plane is not required. FIG. 5 shows an exemplary multi-planar imaging volume obtained at the reference plane of the four-chamber view.

In FIGS. 6-11, 3D multiplanar displays of the fetal heart are shown, with the A (top left), B (top right) and C (lower left) planes respectively representing the three orthogonal planes for the particular standardized plane (A, top left) at study. In each of FIGS. 6-11, plane A represents a standardized fetal heart plane (b-g listed above), and each standardized plane (A) shown in FIGS. 6-11 is a plane that has been generated, using the mathematical relationships described in Equations (1)-(9) above, from the volume displayed in FIG. 5.

FIG. 12 shows exemplary planes generated in accordance with the techniques described with regard to Table 1. In particular, FIG. 1202 represents an axial plane of the abdomen at level of the fetal stomach (shifted 13.7 mm from the four-chamber view), and FIG. 1204 shows the four-chamber view. FIG. 1206 shows the left ventricular outflow tract (shifted 3.8 mm from the four-chamber view), FIG. 1208 shows the right ventricular outflow tract (PA) (shifted 8.7 mm from the four-chamber view), and FIG. 1210 shows the three vessel view (shifted 10.2 mm from the four-chamber view). At step 5 in FIG. 2, images can also be automatically displayed in real time (or near real time), or displayed in a cineloop of a cardiac cycle with appropriate equipment.

In at least one embodiment of the invention, each of the standardized planes can be displayed automatically subsequent to acquisition of a reference plane within a volume. Once the mathematical and spatial relationships of the standardized volumes for a particular organ are established, then any standardized plane can serve as a reference plane (e.g., the aortic arch of the fetal heart). This is useful in obstetrical ultrasonography, given that the fetus may be in an orientation within the uterus allowing for only the aortic arch to be imaged on 2D ultrasonography. One or more embodiments of the invention can then automatically display other standardized planes, such as the four-chamber view. Standardized planes can also be displayed for fetal organs other than the heart, as well as neonatal and adult organs.

In at least one embodiment of the invention, an image volume can be acquired with advanced transducers, and one or more planes of interest for a particular organ can be automatically displayed in real time upon acquisition. That is, the standard A, B and C planes do not need to be displayed prior to displaying one or more of the standard reference planes of interest. One or more reference planes of interest for a particular organ can thus be displayed directly from, and subsequent to, volume acquisition.

Due to the relatively small size of the fetus, 3D and 4D ultrasound obstetrical imaging allows for acquisition of multiple organs within a single 3D volume. For example, a single 3D volume of the fetal chest generally contains the heart, great vessels, venous connections to the heart and both lungs. At least one embodiment of the present invention therefore contemplates for a comprehensive, or substantially comprehensive, diagnosis or assessment of the fetal cardiovascular system from a single 3D volume. When a volume that contains the entire fetus is acquired, the fetus can be re-oriented in a standardized, referenced position within the acquired volume. Then, any or all ultrasonographic standardized planes can be displayed, optionally automatically, to enable, for example, a physician to evaluate the fetal anatomy (e.g., head, chest, abdomen and/or extremities). Adult and neonatal organs can also be diagnosed in this manner.

At step 6, one or more embodiments of the present invention can utilize, for example, standard (e.g., off-the-shelf) image recognition software to assess the level of the standardized planes and diagnose, or facilitate diagnosis of, an imaged organ. For example, gray scale pattern recognition can be used to ensure proper orientation of automatically generated standardized planes and to compare a specific image (e.g., of and/or within the fetal heart) to one or more respective reference images. The gray scale pattern recognition comparison can be used to identify, for example, normal and abnormal anatomical structures and/or portions thereof. In the case of the fetal heart, the size of ventricles and/or outflow tracts can be compared with one or more corresponding reference images of ventricles and/or outflow tracts. A report can be generated that provides, for example, an indication of normal and abnormal relationships. One or more embodiments of the present invention can thus determine the location of fetal cardiac structures, such as the ventricles and/or the great vessels, and optionally provide data pertaining, for example, to the size and/or shape of structures and relative relationships. Adult and neonatal organs can also be diagnosed in this manner.

FIGS. 13A-16 show A, B, and C plane displays generated from a standardized volume of a fetal heart at approximately 19 weeks of gestation. Planes A (top left), B (top right) and C (lower left) respectively represent the three orthogonal planes (axial (or transverse), sagittal, and coronal) for the particular standardized plane (A, top left) at study. More particularly, in each of FIGS. 13A-16, plane A represents a standardized fetal heart plane (plane of acquisition), and planes B and C represent the two orthogonal planes to the reference plane (plane A).

FIG. 13A shows an initial multiplanar view of a 3D ultrasound volume of the fetal chest at approximately 19 weeks of gestation, obtained at the level of the four-chamber view.

FIG. 13B shows a 3D volume in FIG. 13A, magnified and standardized in plane A. In FIG. 13B, Z rotation was applied to plane A until the spine is located at the 6 o'clock position, as shown at 1302.

In accordance with one or more embodiments of the present invention, standardization of display of 3D volumes should be applied in planes A, B, and C in order to ensure uniformity of orientation in three dimensions. For volumes involving the chest of the fetus, I have discovered that standardization is best achieved by ensuring a uniform orientation of the spine in planes A, B, and C for chest and abdominal volumes. For fetuses in cephalic presentations, this is accomplished by rotating plane A about the Z-axis (Z rotation) in order to place the spine at the 6 o'clock position, and the apex of the heart in the left upper chest. Thus, plane A in FIG. 13A an be rotated approximately 20 degrees clockwise (about the Z-axis), thereby resulting in plane A of FIG. 13B. Planes B and C of FIG. 13B are also respectively rotated approximately 20 degrees with respect to planes B and C shown in FIG. 13A. Although a standardized volume is shown in FIG. 13B, some planes of the fetus may be automatically generated (and displayed) without standardizing plane A and/or B and/or C.

FIG. 14 shows how when the reference point 1402 is moved to the spine in plane A, a longitudinal view of the spine in plane B is provided, and a vertical view of the spine in plane C is provided.

Figure 15:
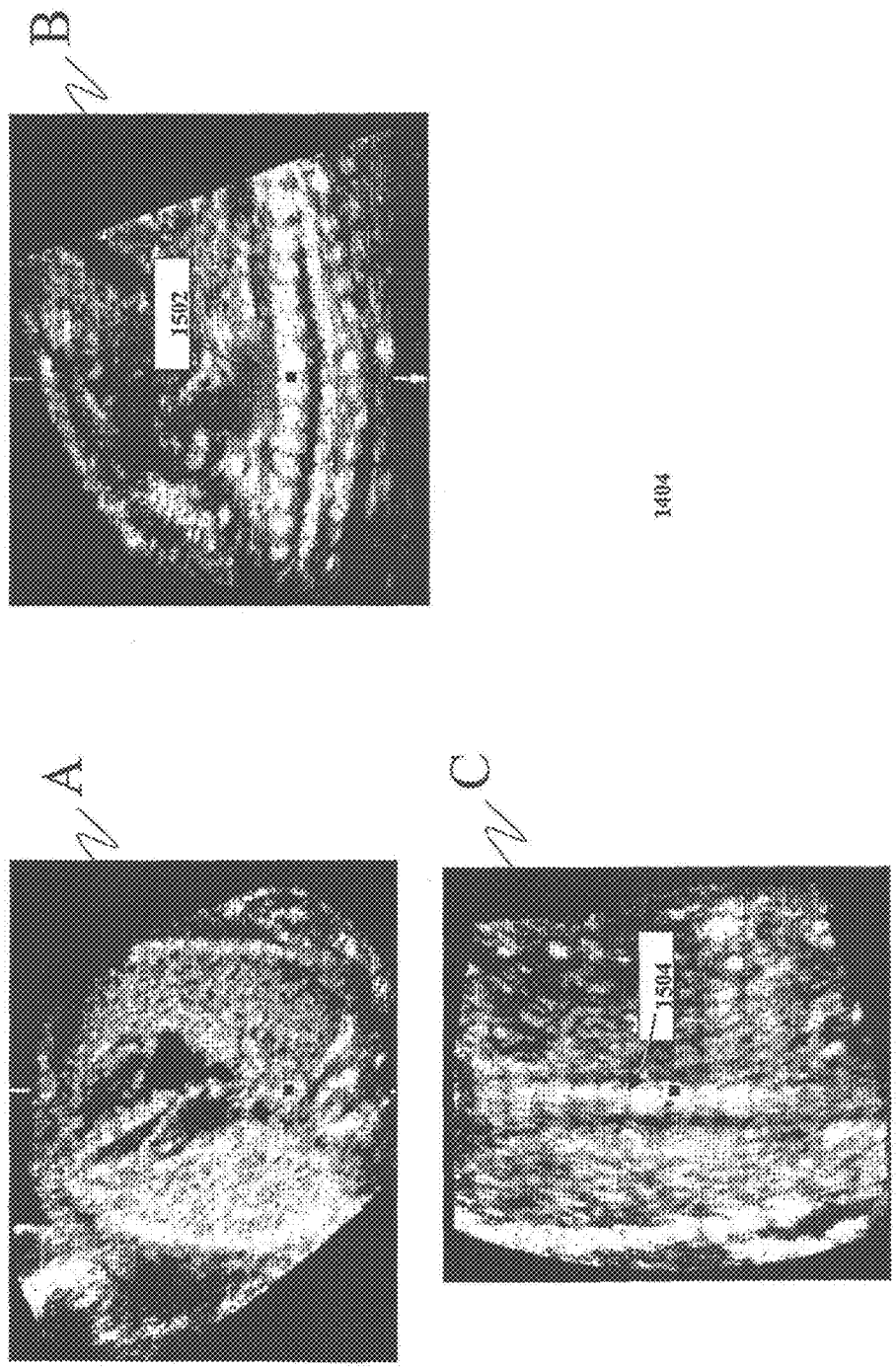
FIG. 15 shows rotation about the Z-axis applied to planes B and C, and resulting alignment of the mid-thoracic spine horizontally in plane B and vertically in plane C.
Figure 17:
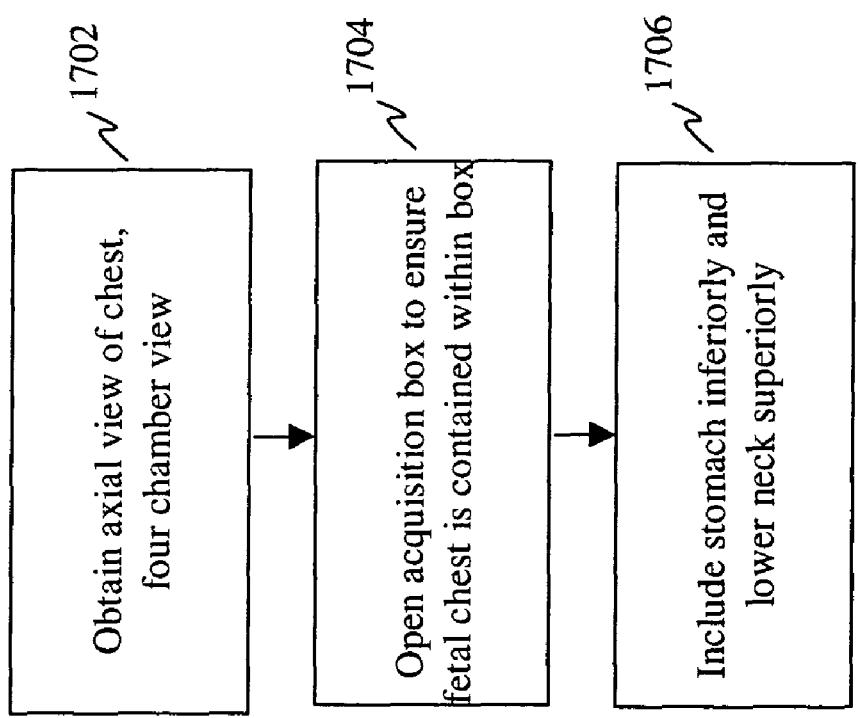
FIG. 17A is a flow diagram of an exemplary method in accordance with the present invention for acquiring a volume of a fetal chest.
FIG. 17B is a flow diagram of an exemplary method in accordance with the present invention for displaying a volume of a fetal chest.
Figure 17:
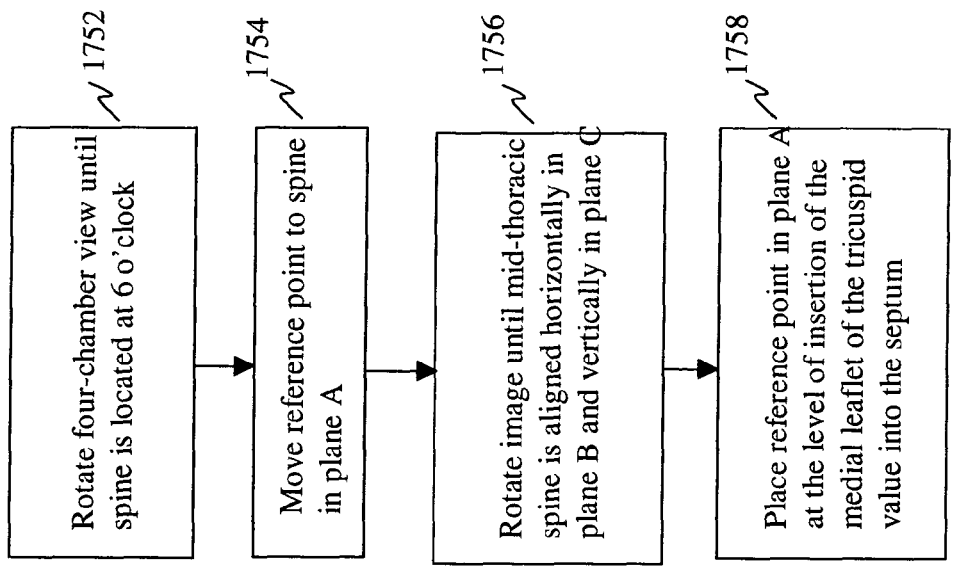

FIG. 15 shows, with respect to FIG. 14, a rotation about the Z-axis applied to planes B and C, and a resulting horizontal alignment 1502 of the mid-thoracic spine in plane B, and vertical alignment 1504 of the mid-thoracic spine in plane C. Standardization in planes B and C is achieved when the spine is aligned substantially horizontally and vertically in planes B and C respectively (Z rotation in each plane).

FIG. 16 shows the reference point 1602 in plane A that is moved to the crux of the heart, at the level of the insertion of the tricuspid valve leaflet into the septum. In accordance with an embodiment of the present invention, a reference point is placed at the crux of the heart in plane A for volumes of the fetal chest.

FIG. 17A shows a diagram of an exemplary method of acquiring a volume of a fetal heart when the fetal heart is in the cephalic presentation. At step 1702, an axial view of the chest at level of the four-chamber view is obtained. One full rib of the fetus should be captured on each side, as shown in FIG. 13A, plane A.

At step 1704, the acquisition box is opened wide enough to ensure that the fetal chest is contained within the box. The box boundaries should be placed just outside the fetal skin. At step 1706, an acquisition angle should be wide enough to include the stomach inferiorly and the lower neck superiorly, as shown in FIG. 13A, plane B.

FIG. 17B shows a diagram of an exemplary method of displaying a volume of a fetal heart. At step 1752, an image in plane A (e.g., a four-chamber view image) is rotated about the Z-axis until the spine is at the 6 o'clock position and the apex of the heart in the left upper chest. This is shown as plane A of FIG. 13B, which results when FIG. 13A is rotated.

At step 1754, the reference point in plane A is moved to the spine (body of vertebra), as is shown in plane A of FIG. 14, at 1402. This will bring a longitudinal view of the spine in plane B, and a vertical view of the spine in plane C, as is shown in FIG. 14, planes B and C.

At step 1756, the image in plane C (coronal view) and plane B (longitudinal view) are rotated about the Z-axis until the section of the mid-thoracic spine is aligned vertically, as is shown in FIG. 15, at 1504, and the section of the mid-thoracic spine in plane B (posterior to the heart) is aligned horizontally, as is shown in FIG. 15 at 1502. At step 1758, the reference point in plane A 1602 (FIG. 16) is placed at the crux of the heart, at the level of the insertion of the medial leaflet of the tricuspid valve into the septum. For breech presentations, the 3D volume can be rotated 180 degrees about the Y-axis prior to performing steps 1752-1758.

FIGS. 18-22 show A, B, and C plane displays generated from a standardized volume of a fetal abdomen at approximately 20 weeks of gestation. Planes A (top left), B (top right) and C (lower left) respectively represent the three orthogonal planes (axial (or transverse), sagittal, and coronal) for the particular standardized plane (A, top left) at study. More particularly, in each of FIGS. 18-22, plane A represents a standardized fetal abdominal (plane of acquisition), and planes B and C represent the two orthogonal planes to the reference plane (plane A).

For fetal abdominal volumes, the reference plane may be obtained as an axial plane of the fetal abdomen at the level of the anatomic landmarks of the abdominal circumference. The reference point can be placed in the center of the abdomen (center of plane A), and the lumbar spine can be used to standardize the display as described for the 3D volumes of the fetal chest. In many fetuses, spinal curvatures exist in the lumbar and sacral regions. These spinal curvatures, when excessive, can make standardization of acquisition and display of abdominal volumes difficult. Given that abdominal and pelvic organs are anatomically simple, the clinical impact of the spinal curvatures on the retrieval of anatomic 2D planes out of a 3D volume of the abdomen is minimal.

More particularly, FIG. 18 shows an initial multiplanar view of a 3D ultrasound volume of the fetal abdomen at approximately 20 weeks of gestation. FIG. 19 shown the 3D volume of FIG. 18, magnified and standardized in plane A. In FIG. 19, a Z rotation was applied to plane A until the spine is located at 6 o'clock, as is generally shown by the white circle in plane A.

FIG. 20 shows how when the reference point shown at the white dot pointed to by the arrow is moved to the spine in plane A, a longitudinal view of the spine in planes B and vertical view in plane C is provided.

FIG. 21 shows, with respect to FIG. 20, a rotation about the Z-axis applied to planes B and C, aligning the lumbar spine horizontally in plane B and vertically in plane C. The white arrow heads point to the lumbar spine in planes B and C. In FIG. 22, the reference point in plane A, pointed to by and proximate the arrow head in plane A, is moved to the center of the abdomen.

Figure 23A:
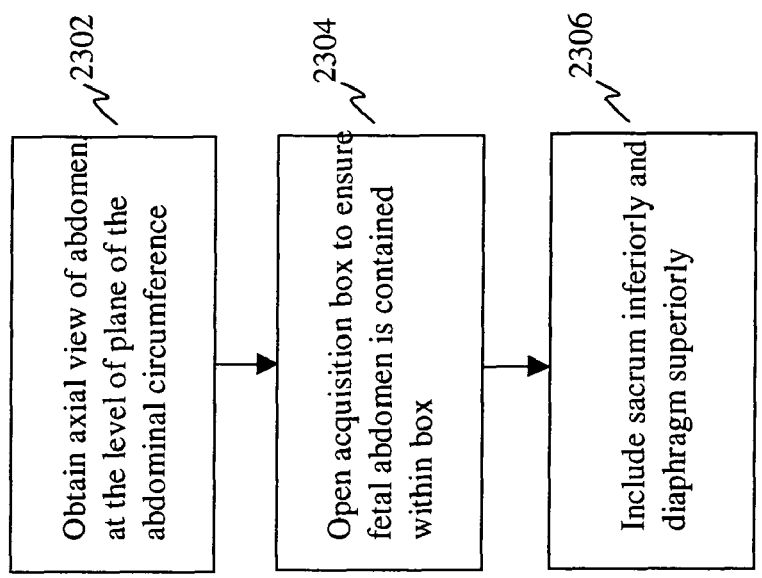
FIG. 23A is a flow diagram of an exemplary method in accordance with the present invention for acquiring a volume of a fetal abdomen.

FIG. 23A shows a diagram of an exemplary method of acquiring a volume of a fetal abdomen. At step 2302, an axial view of the abdomen at level of the plane of the abdominal circumference is obtained. One full rib of the fetus should be captured on each side, as is shown in FIG. 18A.

At step 2304, the acquisition box is opened wide enough to ensure that the fetal abdomen is contained within the box. The box boundaries should be placed just outside the fetal skin, as is shown in FIG. 18A. At step 2306, an acquisition angle should be wide enough to include the sacrum inferiorly and the diaphragm superiorly, as is shown in FIG. 18B.

Figure 23B:
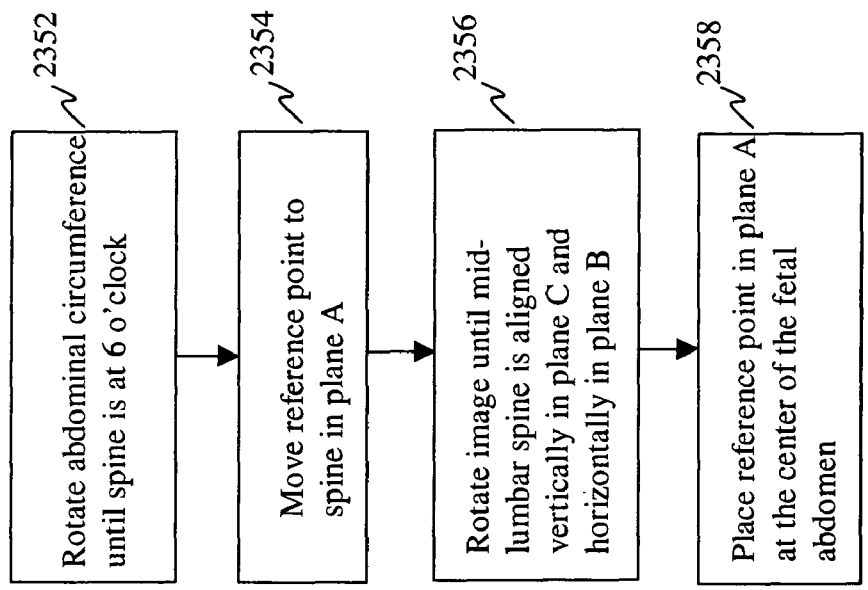
FIG. 23B is a flow diagram of an exemplary method in accordance with the present invention for displaying a volume of a fetal abdomen.

FIG. 23B shows a diagram of an exemplary method of displaying a volume of a fetal abdomen. At step 2352, an image in plane A (e.g., abdominal circumference) is rotated about the Z-axis until the spine at 6 o'clock, and the stomach in the left abdomen, as is shown in FIG. 19, plane A.

At step 2354, the reference point in plane A is moved to the spine (body of vertebra) when the spine is in the 6 o'clock position, as shown in FIG. 20, plane A. This will bring a longitudinal view of the spine in plane B, and a vertical view in plane C, as is respectively shown in FIG. 20, planes B and C.

At step 2356, the image in plane C (coronal view) is rotated about the Z-axis until the section of the mid-lumbar spine is aligned substantially vertically, as is shown in FIG. 21, plane C, and the image in plane B is rotated about the Z-axis until the mid-lumbar spine is aligned substantially horizontally, as is shown in FIG. 21, plane B. At step 2358, the reference point in plane A is placed at the center of the fetal abdomen, as shown in FIG. 22, plane A. For breech presentations, the 3D volumes can be rotated 180 degrees about the Y-axis prior to performing steps 2352-2358.

FIG. 24 shows an initial 3D ultrasound volume of the fetal head at the level of the lateral ventricles, obtained at approximately 18 weeks of gestation, in a fetus in left occiput cephalic presentation. Plane A represents the axial view, plane B the coronal view and plane C represents the sagittal view of the central nervous system. In the multiplanar display of 3D volumes obtained from fetuses in cephalic presentations, the sagittal view of the central nervous system is displayed in an inverted image with the top of the head at the bottom of the image (FIG. 24, plane C).

FIG. 25 shows the same 3D volume that is displayed in FIG. 24, subsequent to plane A in FIG. 24 being rotated about the Y and Z axes. The rotation about the Y-axis of 180 degrees in plane A flips the orientation of the sagittal view of the fetal head in plane C to its customary orientation with the top of the head in the superior aspect of the image. The Z rotation orients the 3D volume with the frontal part of the brain to the right from an observer's point of view. The resulting orientation is shown in FIG. 25. Accordingly, for breech presentations, only rotation about the Z-axis to orient the 3D volume with the frontal part of the brain to the right from an observer's point of view is needed.

Figure 26:
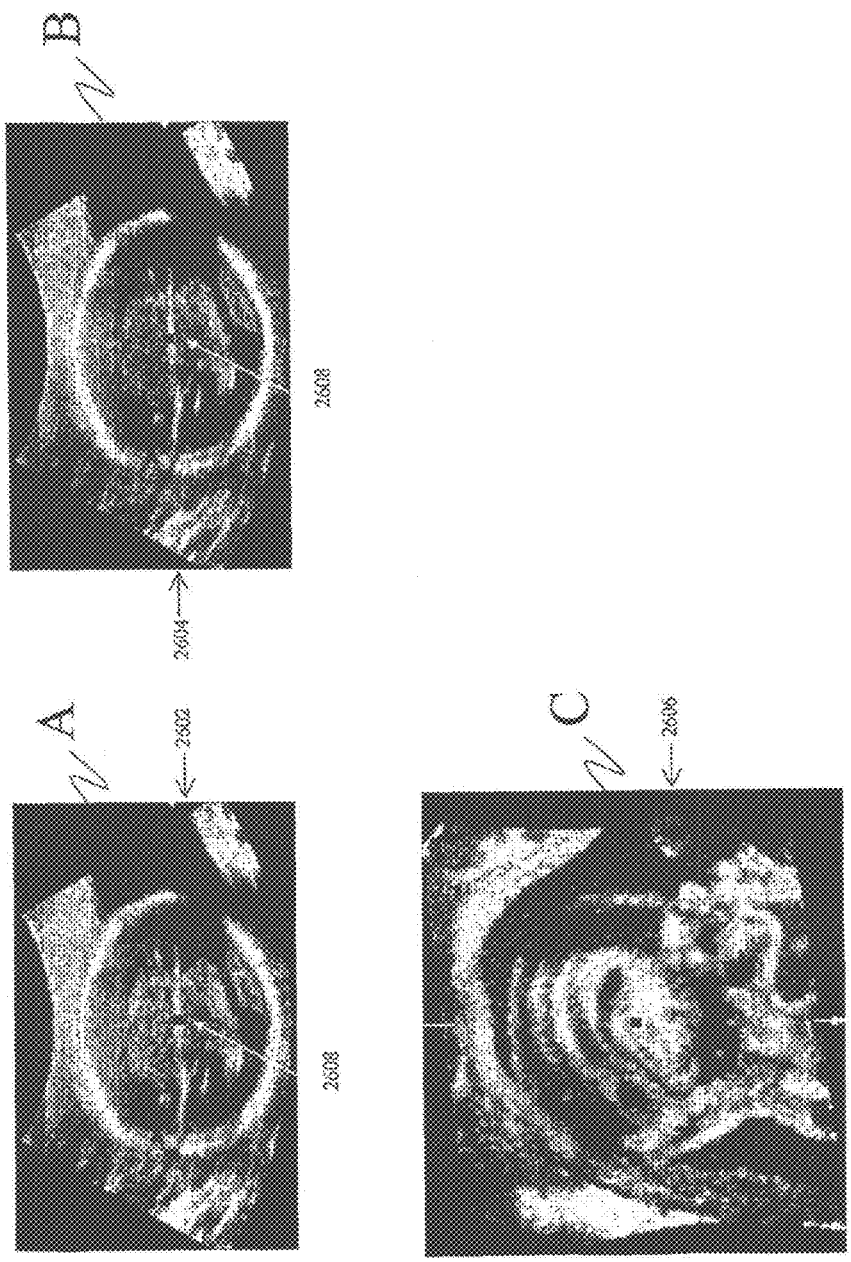
FIG. 26 shows a standardization completed with the horizontal alignment of the inter-hemispheric fissure in planes A and B, and a military position of the fetal face in plane C.

For volumes involving the fetal central nervous system, such as shown in FIGS. 24-26, a plane obtained at an axial view of the fetal head at the level of the lateral ventricles can serve as the reference plane (FIG. 24, plane A). The inter-hemispheric fissure can be used for standardization in planes A and B, and the position of the fetal face in plane C (FIG. 26).

In 3D volumes obtained from fetuses in breech presentations, the sagittal plane (FIG. 24, plane C) would be displayed in the customary anatomic orientation with the top of the head in the superior aspects of the image.

FIG. 26 shows a standardization completed with the horizontal alignment of the inter-hemispheric fissure in planes A and B (shown at 2602, 2604), and a military position of the fetal face in plane C (shown at 2606). Finally, the reference point is placed in the mid-point of the inter-hemispheric fissure in plane A 2608 (the reference point 2608 is also shown in plane B).

Figure 27A:
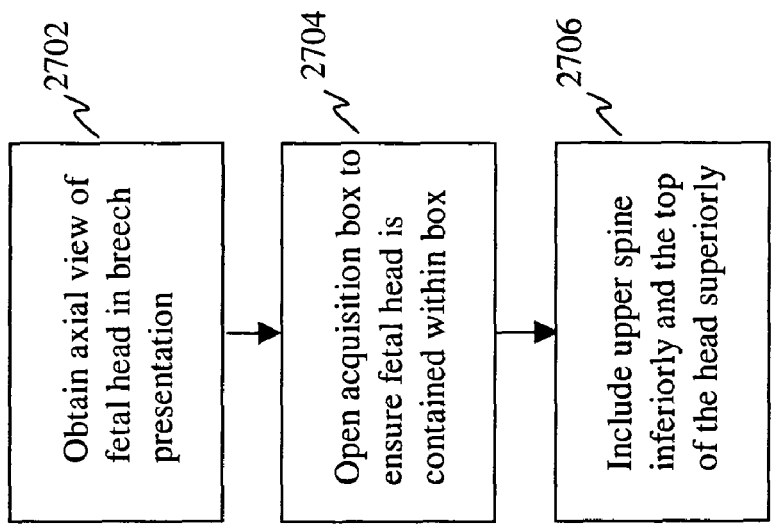
FIG. 27A is a flow diagram of an exemplary method in accordance with the present invention for acquiring a volume of a fetal head.

FIG. 27A shows a diagram of an exemplary method of acquiring a volume of a fetal head, in breech presentation. At step 2702, an axial view of the head at the plane of the level of the lateral ventricles is obtained, as is shown in FIG. 24, plane A.

At step 2704, the acquisition box is opened wide enough to ensure that the fetal head is contained within the box. The box boundaries should be placed just outside the fetal skull, as is shown in FIG. 24, plane A. At step 2706, an acquisition angle should be wide enough to include the upper spine inferiorly and the top of the head superiorly, as is shown in FIG. 25, plane C.

Figure 27B:
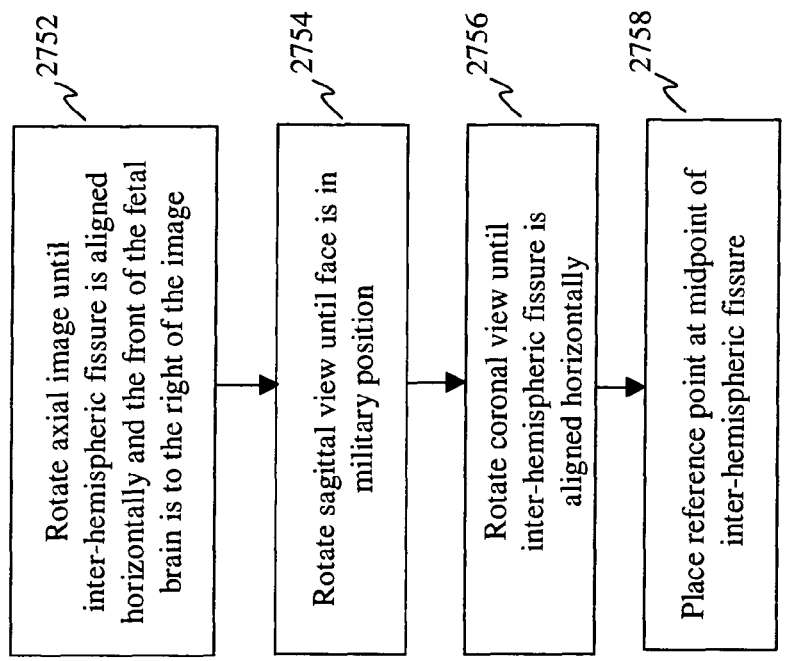
FIG. 27B is a flow diagram of an exemplary method in accordance with the present invention for displaying a volume of a fetal head.

FIG. 27B shows a diagram of an exemplary method of displaying a volume of a fetal head. At step 2752, an image in plane A is rotated about the Z-axis until the inter-hemispheric fissure is aligned horizontally and the frontal part of the fetal brain is to the right of the image, from an observer's view point. This is shown in FIG. 26, plane A.

At step 2754, the image in plane C (sagittal view) is rotated about the Z-axis until the fetal face is in a military position (fetus with straight plane of sight). This is shown in FIG. 26, plane C.

At step 2756, the image in plane B (coronal view) is rotated along the Z-axis until the inter-hemispheric fissure is aligned horizontally. This is shown in FIG. 26, plane B. At step 2758, the reference point in plane A is placed at the midpoint of the inter-hemispheric fissure. This is shown in FIG. 26, plane A.

The many features and advantages of the invention are apparent from the detailed specification, and thus, it is intended to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention. While the foregoing invention has been described in detail by way of illustration and example of preferred embodiments, numerous modifications, substitutions, and alterations are possible.

What is claimed is:

1. A method for utilizing sonography equipment to acquire and display at least one anatomic plane of an organ, comprising:
    moving an ultrasonic transducer to obtain an ultrasound image of a reference anatomic plane of the organ; and
    using at least one predetermined spatial mathematical relationship, wherein the predetermined spatial mathematical relationship is determined using at least a regression model of gestational age, and relating the reference anatomic plane and the at least one anatomic plane to retrieve and display the at least one anatomic plane.

2. The method of claim 1, wherein the organ is a fetal heart.

3. The method of claim 2, wherein the reference anatomic plane comprises at least one of a pulmonary artery, a three vessel view, a left ventricular outflow tract, a ductal arch, a venous connection, and an aortic arch.

4. The method of claim 2, wherein at least two opposing sides of an image acquisition boundary are respectively placed outside a first surface and a second surface of fetal skin.

5. The method of claim 4, wherein at least one rib of a fetus appears on opposing sides of the image acquisition boundary.

6. The method of claim 5, further comprising utilizing an acquisition angle sufficiently wide so an image within the image acquisition boundary comprises a view of the stomach inferiorly and the lower neck superiorly of the fetus.

7. A method for utilizing sonography equipment to acquire and display an ultrasound image of a fetal abdomen, comprising:
    moving an ultrasonic transducer to obtain an ultrasound image of an axial view of a fetal abdomen at a level of a anatomic plane of an abdominal circumference;
    opening an acquisition box of the image so the fetal abdomen is contained within the box;
    utilizing an acquisition angle sufficiently wide so the acquired image data comprises a view of a sacrum inferiorly and a diaphragm superiorly; and
    using at least one predetermined spatial mathematical relationship, wherein the predetermined spatial mathematical relationship is determined using at least a regression model of gestational age, and relating the anatomic planes to retrieve and display one or more planes of interest of the fetal abdomen.

8. The method of claim 7, wherein at least one rib of the fetus appears on opposing sides of the image.

9. The method of claim 7, wherein at least two opposing sides of the acquisition box boundaries are respectively placed just outside a first surface and a second surface of fetal skin.

10. A method for utilizing sonography equipment to acquire and display an ultrasound image of a fetal head, comprising:
    moving an ultrasonic transducer to obtain an ultrasound image of an axial view of a fetal head at a level of a anatomical plane of a level of lateral ventricles;
    opening an acquisition box of the image so the fetal head is contained within the box;
    utilizing an acquisition angle sufficiently wide so the acquired image data comprises a view of an upper spine inferiorly and a top of the fetal head superiorly; and
    using at least one spatial predetermined mathematical relationship, wherein the predetermined spatial mathematical relationship is determined using at least a regression model of gestational age, and relating the anatomic planes to retrieve and display one or more planes of interest of the fetal head.

11. The method of claim 10, wherein at least two opposing sides of the acquisition box boundaries are respectively placed just outside a first surface and a second surface of a fetal skull.

12. A method for utilizing sonography equipment to acquire and display at least one anatomic plane of a neonatal organ, comprising:
    moving an ultrasonic transducer to obtain an ultrasound image of a reference anatomic plane of the neonatal organ; and
    using at least one predetermined spatial mathematical relationship, wherein the predetermined spatial mathematical relationship is determined using at least a regression model of gestational age, and relating the reference anatomic plane and the least one anatomic plane to retrieve and display the at least one anatomic plane of the neonatal organ.

13. The method of claim 12, wherein the neonatal organ is a head.

14. A method for utilizing sonography equipment to acquire and display at least one anatomic plane of a three dimensional ultrasound image in real time, comprising:

moving an ultrasonic transducer to obtain an ultrasound image of a reference anatomic plane of an organ; and using at least one predetermined spatial mathematical relationship, wherein the predetermined spatial mathematical relationship is determined using at least a regression model of gestational age, and relating the reference anatomic plane and the at least one anatomic plane to retrieve and display in real time the at least one anatomic plane.

* * * * *